(12) United States Patent
Laub et al.

(10) Patent No.: US 6,866,848 B2
(45) Date of Patent: Mar. 15, 2005

(54) ANTIGENIC POLYPETIDE SEQUENCE OF FACTOR VIII, FRAGMENTS AND/OR EPITOPES THERE OF

(75) Inventors: Ruth Laub, Brussels (BE); Mario Di Giambattista, Brain-le-Comte (BE)

(73) Assignee: Croix-Rouge de Belgique, Brussels (BE)

( * ) Notice: Subject to any disclaimer, the term of this patent is extended or adjusted under 35 U.S.C. 154(b) by 20 days.

(21) Appl. No.: 08/765,837

(22) PCT Filed: Jul. 14, 1995

(86) PCT No.: PCT/BE95/00063

§ 371 (c)(1),
(2), (4) Date: Sep. 7, 1999

(87) PCT Pub. No.: WO97/01516

PCT Pub. Date: Jan. 16, 1997

(65) Prior Publication Data

US 2003/0147900 A1 Aug. 7, 2003

(30) Foreign Application Priority Data

Jul. 14, 1994 (BE) .............................. 09400666

(51) Int. Cl.⁷ .............................. A61K 39/00
(52) U.S. Cl. .............. 424/185.1; 424/195.11; 514/12; 514/16; 530/324; 530/329

(58) Field of Search .................. 424/185.1, 195.11; 514/12, 16; 530/324, 329, 300, 381

(56) References Cited

U.S. PATENT DOCUMENTS 4,965,199 A * 10/1990 Capon et al.

OTHER PUBLICATIONS

Vehar et al., Nature 312:337–342, 1984.*
Van Regenmortel. Methods: A Companion to Method of Enzymology, 9:465–472, 1996.*
Palmer et al., Vox Sang. 72:148–161, 1996.*

* cited by examiner

*Primary Examiner*—Patrick J. Nolan
(74) *Attorney, Agent, or Firm*—Knobbe, Martens, Olson & Bear, L.L.P.

(57) ABSTRACT

An antigenic polypeptide of factor VIII comprises a polypeptide included between the Glutamic Acid 1649 and Asparagine 2019, preferably between Arginine 1652 and Arginine 1917 of the polypeptide of factor VIII, or a polypeptide included between Alanine 108 and Methionine 355, or a polypeptide included between Aspartic Acid 403 and Aspartic Acid 725, or a polypeptide included between Lysine 2085 and Lysine 2249.

19 Claims, 6 Drawing Sheets

ANTIGENIC POLYPETIDE SEQUENCE OF FACTOR VIII, FRAGMENTS AND/OR EPITOPES THERE OF

CROSS-REFERENCE TO RELATED APPLICATIONS

This application is the U.S. National Phase under 35 U.S.C. §371 of International Application PCT/BE95/00063, filed Jul. 14, 1995, which claims priority to Belgian application BE 9400666, filed Jul. 14, 1994.

SUBJECT OF THE INVENTION

The present invention relates to the antigenic polypeptide sequence of factor VIII, to fragments and epitopes of this sequence and to the major parts of these epitopes, to the inhibitors which are directed against this sequence, its fragments, its epitopes and/or the major parts of these epitopes, and to the anti-inhibitors which are directed against the said inhibitors.

The present invention also relates to a pharmaceutical composition and to a diagnostic device comprising the abovementioned molecules.

TECHNICAL BACKGROUND UNDERLYING THE INVENTION

Recently, factor VIII preparations which have been purified from large plasma pools by means of ion exchange chromatography, or very recently by means of immunoaffinity, have been made available to haemophilics in adequate quantities.

Various preparations of FVIII which have been obtained by genetic manipulation are currently under development or under clinical trial. These FVIIIs are either intact molecules or deleted molecules (Bihoreau (1992)).

FVIII is a glycoprotein cofactor of plasma coagulation and acts at the level of factor X (FX) activation. Characterization of FVIII and its mechanism of action is made more difficult because of its low concentration in the plasma, the size heterogeneity and its extreme sensitivity to enzymic degradation. This reaction comprises the proteolysis of FX to form activated factor X (FXa=Stuart factor) and brings into play a complex (Tenase complex) which comprises the enzyme (activated FIX or FIXa), a cofactor (activated FVIII or FVIIIa), calcium ions and phospholipids.

FVIII is a protein which is so complex that, even though the sequence of its gene has been known since 1984 (Vehar et al. 1984 Nature 312, pp. 337–342), neither the complete structure of plasma FVIII (only about 50% of the protein has been sequenced) nor the precise structure of the carbohydrates has yet been established. The DNA sequence has been allowed to define the primary sequence of FVIII (SEQ ID NO: 21) (a rare exception to the instructions laid down by the FDA for the therapeutic products derived from biotechnology).

Nevertheless, subtle differences between plasma FVIII and recombinant FVIII have been identified: i.e. glycosylation, plasma half-life following infusion, etc.

FVIII is in the main synthesized in the hepatocytes. It has been cloned in mammalian cells, insect cells and yeast cells (Webb et al., 1993). These glycoproteins which are produced by biotechnological processes can exhibit differences in the structure and composition of the sugars as compared with the natural protein. The cDNA of FVIII has also been expressed in transgenic sheep (Halter et al., 1993).

The cDNA encodes a polypeptide of 2351 amino acids, including the signal peptide of 19 amino acids which is cleaved off in the endoplasmic reticulum. Post-translational modifications take place in the Golgi apparatus: i.e. glycosylation of the serines and threonines and addition of sulphate ions to the tyrosine residues. Following maturation, the protein is subsequently secreted into the plasma in the form of 2 chains, of 210 kDa (up to residue 1648) and 80 kDa (from residue 1649 to residue 2332), which are joined by a divalent ion, with the lighter chain being linked non-covalently to the von Willebrand factor (vWf) by its N-terminal end (1 molecule of vWf per molecule of FVIII). In the plasma, this complex is stabilized by hydrophobic and hydrophilic bonds in the presence of a 50-fold excess of vWf. This latter is reported to inhibit the attachment of FVIII to phospholipids. The fact that FVIII binds to the platelets has been established, although the presence of specific receptors expressed on the surface of the platelets has not been clearly demonstrated (Nesheim et al., 1993). Following its attachment to the membrane phospholipids, it is reported to unmask high-affinity binding sides for FIXa (Bardelle et al., 1993).

FVIII is made up of three structural domains, A, B and C (Kaufman R J, 1992; Bihoreau et al., 1992) which are arranged in the order A1:A2:B:A3:C1:C2 (FIG. 1). The A domains possess more than 40% homology and are also homologous to ceruloplasmin. 30% homology also exists between the A domains of factor V and FVIII. The C domain occurs twice and is reported to be able to bind glycoconjugates and phospholipids having a net negative charge (Kemball-Cook and Barrowcliffe (1992); Fay, P J, 1993)). It exhibits homology with lectins which are able to bind to negatively charged phospholipids. The platelet attachment site has been located in this region (C2 domain) (Foster et al., (1990)). While domain B, which represents more than 40% of the mass of FVIII, does not have any known specific activity, it could play a subtle role in the regulation of FVIII by protecting it, for example, from the action of thrombin. It does not possess any known homology with other proteins.

It possesses 19 glycosylation sites out of the 25 which have been identified in FVIII. Comparison of the amino acid sequences of human and porcine FVIII reveals major differences within this B region. Nevertheless, porcine FVIII is used effectively for treating haemophilics exhibiting inhibitors. These observations have led to the construction of an FVIII gene from which the part encoding this B region has been deleted and which can be used to produce a deleted recombinant FVIII which is intended for the treatment of haemophilia.

Using immunopurification, different forms of active FVIII have been isolated which all possess a light chain of 80 kDa and whose heavy chain can have a molecular weight of between 210 and 90 kDa. These forms are reported to be derived by progressive degradation of the C-terminal end of the heavy chain. The binding of the two chains is non-covalent and results from a divalent metallic ion (Me++) bond between the responsible residues in domains A1 and A3. After formation of the activated complex (50–45 kDa) (heavy chain having accessible A2 domain) and 70 kDa (light chain), an inactivation phase is observed, probably as a consequence of prolonged contact with thrombin and dissociation of the 50 kDa and 45 kDa fragments. FVIIIa is also inactivated by activated protein C (APC) following proteolysis of the heavy chain. This inactivation is accelerated if the FVIIIa is attached to a phospholipid surface. This down-regulation of the activity of FVIIIa is reported to depend on a phosphorylation by a platelet enzyme (Kalafatis et al., (1990)).

Most of the epitopes which are recognized by the various murine monoclonals which have been isolated to date do not appear to be located in the "functional sites" of FVIII. Some epitopes have been identified which are recognized by antibodies which have an effect on the activity of FVIII (inhibition of the chromogenic and/or clotting tests).

These antigenic determinants consist of fragments 351–365 (A1 domain—heavy chain), 713–740 (A2 domain), 1670–1684 (A3 domain—light chain) (NH$_2$ end of the light chain) or else 2303–2332 (C2 domain—light chain) (Foster C, (1990)), fragments 701–750 (Ware et al. (1989)), 1673–1689 (Leyte et al. (1989)), 330–472, 1694–1782 (EP-0 202 853), 322–740 and 2170–2322 (Scandella et al. (1992)).

The antibodies which recognize these various sites interfere, respectively, with the activation of FVIII, the binding of vWf or the binding of phospholipids.

Other antibodies, which do not inhibit standard activity tests in vitro, can exert an influence on the behaviour of FVIII with the other constituents of the coagulation cascade while attaching themselves to sites in the molecule which are at a substantial distance from the active sites. These antibodies, thus modified, can interfere with the natural state of folding of FVIII by altering some of its properties ("allosteric model").

These mapping experiments make use of peptides which are synthesized by FVIII gene fragments which are cloned into *E. coli* and only provide an approximate idea of the location of the antigenic determinants which are recognized by these monoclonal antibodies. Thus, the sizes of the identified fragments range between 30 and 100 amino acids.

At present, it is necessary to crystallize a protein and analyse it with X rays in order to identify its antigenic sites unambiguously. Unfortunately, no data are available for FVIII, whose high molecular weight is a major handicap with regard to crystallization.

The antigenic regions coincide with the hydrophilic character of these regions: the more the oligopeptide sequence is exposed to the external medium (situated on the surface), the more this part is capable of being recognized in an immune reaction. By contrast, the hydrophobic parts, which are generally situated in the interior of the protein, are not considered to be very antigenic.

Currently, a predominant notion among haemophilic patients, clinicians and "fractionators" is that of having available a purified FVIII which is devoid of all pathogenic plasma contaminants and secondary effects.

However, whether after immunopurification using murine monoclonal antibodies or after obtaining it by genetic recombination in mammalian cells, highly purified FVIII is extremely unstable for reasons which are not apparent. In order to stabilize it, substantial quantities of human plasma albumin are added during the course of purification, such that the final specific activity is of the order of 2–3 U/mg of protein. The same applies to rFVIII which is coexpressed with the von Willebrand factor, which is a natural stabilizer, in CHO cells. These data appear to suggest that the purification steps exert an influence on the FVIII molecule, with these steps being able to interfere with its natural state of folding, to introduce confirmational changes which are more or less stable and to reveal new potential epitopes following infusion into the patient.

According to the authors (Ljung et al. (1992); Sultan et al., (1992); Lorenzo et al. (1992)), one of the serious complications which is seen in from 5 to 50% of the haemophilics who are given multiple therapeutic infusions of FVIII is the appearance of antibodies (inhibitors) which inactivate FVIII and render ineffective any subsequent injection of FVIII.

The spontaneous appearance of autoantibodies having a pathological anti-FVIII activity is rare in non-haemophilics (prevalence: $10^{-5}$) and has been reported in elderly individuals, in those exhibiting immunological disorders and in post-partum individuals (Kessler (1991), Hultin (1991)). A multi-centre study which was carried out on 3,435 haemophilic patients shows that all the age groups are affected, including patients of less than 5 years old. The majority (82%) display a very high response (>10 BU) (Sultan et al. (1992)). While these anti-FVIII antibodies have been reported to consist essentially of IgG antibodies of the IgG4 type, IgG2 (Gilles et al. (1993)b), IgA and IgM antibodies have also been described (Lottenburg et al. (1987))). They react weakly with purified heterologous FVIII molecules from other mammals (Bennett, B et al. (1972)). At the present time, it is not known what induces the appearance of the inhibitors in some haemophilics. If there is an association between the severity of the deletion of the gene and the development of an immune response which no longer recognizes FVIII as a self protein, this association is only demonstrated in a minority of patients. It has not been possible to demonstrate any specific host susceptibility which is linked to genetic markers, such as, for example, a preferential association with certain determinants of the MEC class II complex (Hoyer (1991)), without a doubt because not all the FVIII epitopes which are recognized by specific antibodies have yet been determined. It also appears that the different methods of preparing FVIII could exert an influence on its structure, its physicochemical properties or its natural microenvironment (Vermeylen, J and Peerlinck (1991); Gomperts, et al. (1992); Peerlinck et al. (1993)). Barrowcliffe et al. (1983) have demonstrated that phospholipids protect the procoagulatory activity from inactivation by specific human antibodies. The presence of natural anti-FVIII antibodies in 17% of healthy donors (screening carried out on 500 plasma donations) without any pathological symptoms demonstrates the importance of becoming better acquainted with the three-dimensional structural appearance assumed by physiological FVIII (Ciavarella and Schiavoni (1992)).

Transfusion which has been studied on mixed lymphocyte cultures, in animal models and during clinical trials has demonstrated modification of the immuno-modulation in the transfused subject, inducing an allo-immunization and also a down-regulation of some immune functions. It expresses itself in the form of suppressor cells, anti-idiotype antibodies or a decrease in NK cells. It is as if a certain degree of tolerance was being induced. These effects can be reversed by infusing interleukin 2 (IL-2) (Triulzi et al., 1990). In vitro, an inhibitory effect on the secretion of IL-2 as well as the proliferation of peripheral blood mononuclear cells are obtained in the presence of a cryoprecipitate or relatively impure preparations of FVIII (from 0.5 to 10 U/mg of protein) (Madhok et al., 1991; Wadhwa, M et al., 1992). These effects are not observed in the presence of rFVIII or FVIII which have been purified by immunoaffinity. This latter preparation is reported to have an activating effect on T cells (Madhok et al., 1991). However, it is not possible to extrapolate these findings directly to an in vivo situation.

No experimental model exists which makes it possible to forecast the immunogenicity or the immuno-modulatory effect of the FVIII preparations, or the susceptibility of the host, before they have been administered clinically. This model becomes an absolute necessity in the face of the increase in the frequency of the appearance of anti-FVIII antibodies in current clinical trials which make use of FVIII preparation which are of very high specific activity and which have been obtained either by immunopurification or by DNA manipulation techniques (Seremetis et al. (1991)). In addition, Aledorf (1993) has demonstrated that when these two types of preparation are used in naive subjects who have not previously been transfused (PUPS), an inhibitor prevalence is observed which amounts to up to 27%.

STATE OF THE ART

Patients who develop an anti-FVIII immune response find themselves in a serious situation which necessitates the use of severe, aggressive and excessively expensive measures. One of the most frequently employed techniques is to swamp the organism with regular injections of very high doses of FVIII (from 100 to 200 U/kg/day) (Ewing et al. (1988)) in association with a concentrated prothrombin complex (FEIBA) (Bonn's protocol), a procedure which effectively reduces the level of inhibitors in the blood (Sultan et al. 1986). In addition, this type of treatment has to be continued for a very long time (Lian et al., 1989). Trials carried out using smaller doses of FVIII have met with a certain degree of success in patients whose anti-FVIII antibody levels are much lower (Gruppo, (1991)).

An alternative approach is to use FVIII from a non-human species such as the pig, which FVIII is not neutralized by the anti-FVIII of the patient and enables haemostasis to take place. While a multi-centre study has shown the advantages of such a treatment, it has also demonstrated that anti-porcine FVIII antibodies are formed (Lozier (1993); Moreau et al. (1993); Hay and Bolton-Maggs (1991); Clyne et al. (1992)). Activated factor VIII, obtained by recombinant DNA technology, has also been employed as an alternative means for achieving coagulation in patients who exhibit inhibitors (Ingerslev et al. (1991)).

Recently, a profitable strategy (Nilsson et al. (1990)) for reducing the level of inhibitors has consisted in subjecting patients to an extracorporeal circulation to enable solid-phase absorption of the total IgG to be effected on protein A while at the same time treating the patients with cytostatic agents such as cyclophosphamide.

The infusion of polyvalent intravenous immunoglobulins (IVIG), where appropriate combined with an immunosuppressive treatment, has been found to be relatively effective, although the reason for this effectiveness is still not fully established. Various hypotheses involving feed-back inhibition of IgG synthesis, stimulation of IgG clearance or activation of T suppressor cells have been advanced (Bloom (1992)). An interesting explanation is that these commercial intravenous immunoglobulins might contain antibodies which are able to react with the variable parts (idiotypes) of the anti-FVIII antibodies and neutralize these antibodies. It is suggested that this anti-idiotype activity might be specific to each donor and could be synergistic within an IgG pool (Dietrich et al. (1992)).

Unfortunately, none of these approaches has been found to be satisfactory in terms of safety, efficiency and cost.

OBJECTS OF THE INVENTION

The present invention is aimed at obtaining an antigenic polypeptide sequence of factor VIII, and fragments and epitopes of this sequence, whose purpose is to improve the diagnosis and/or therapy of immune disorders, in particular those induced by inhibitors of FVIII and inhibitors of the binding of FVIII to the von Willebrand factor (vWf) and/or to membrane phospholipids (PL).

Another object of the invention is aimed at obtaining inhibitors which exhibit an immunoaffinity with this antigenic polypeptide sequence, its fragments and/or its epitopes, whose purpose is also to improve the diagnosis and/or therapy of immune disorders.

A supplementary object is aimed at obtaining anti-inhibitors, in particular antibodies, which are directed against the abovementioned said inhibitors and whose purpose is to improve the diagnosis and/or therapy of immune disorders.

CHARACTERISTIC ELEMENTS OF THE INVENTION

Figure 1:
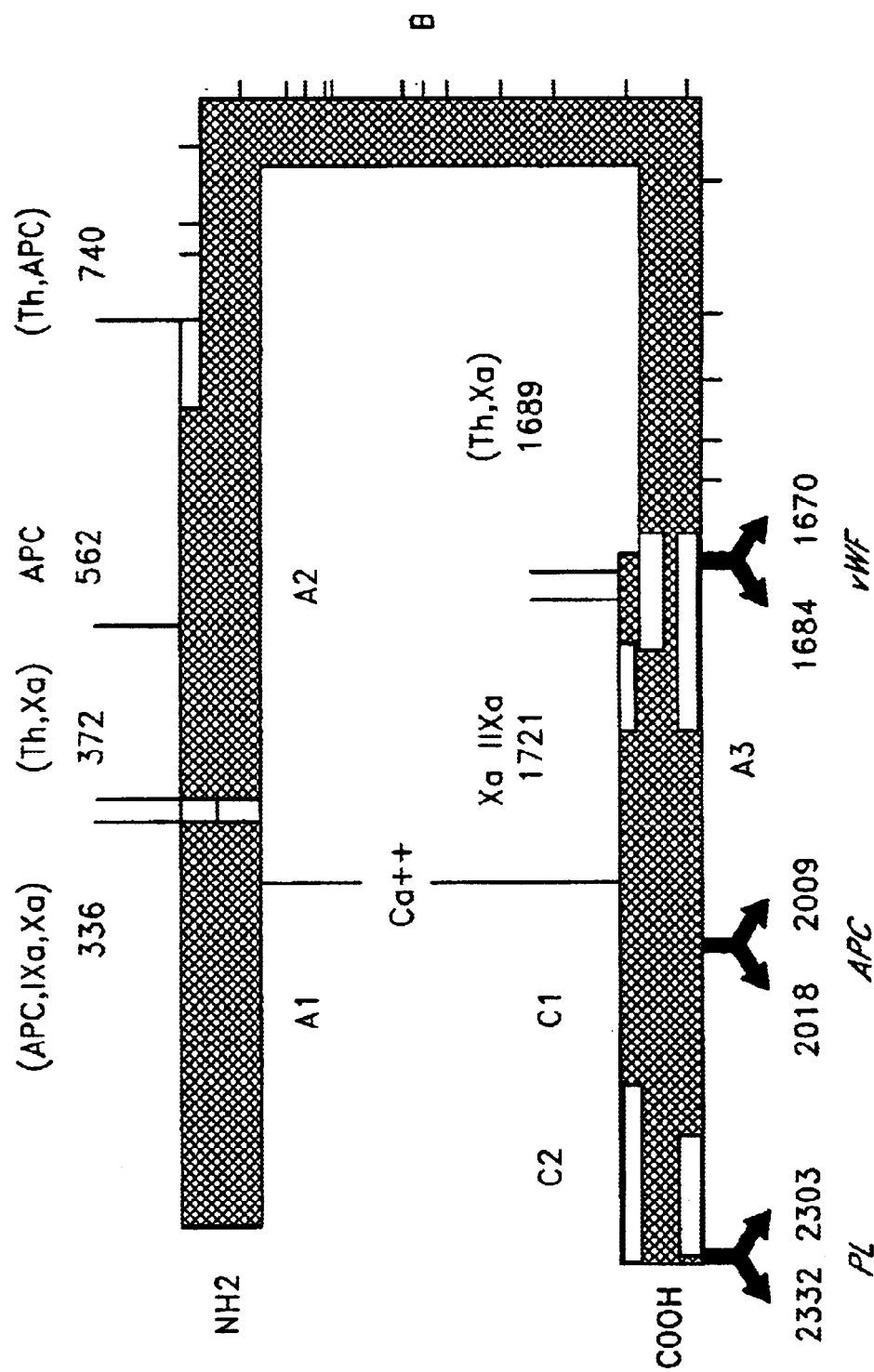
FIG. 1 diagrammatically depicts the polypeptide sequence of factor VIII.
Figure 2:
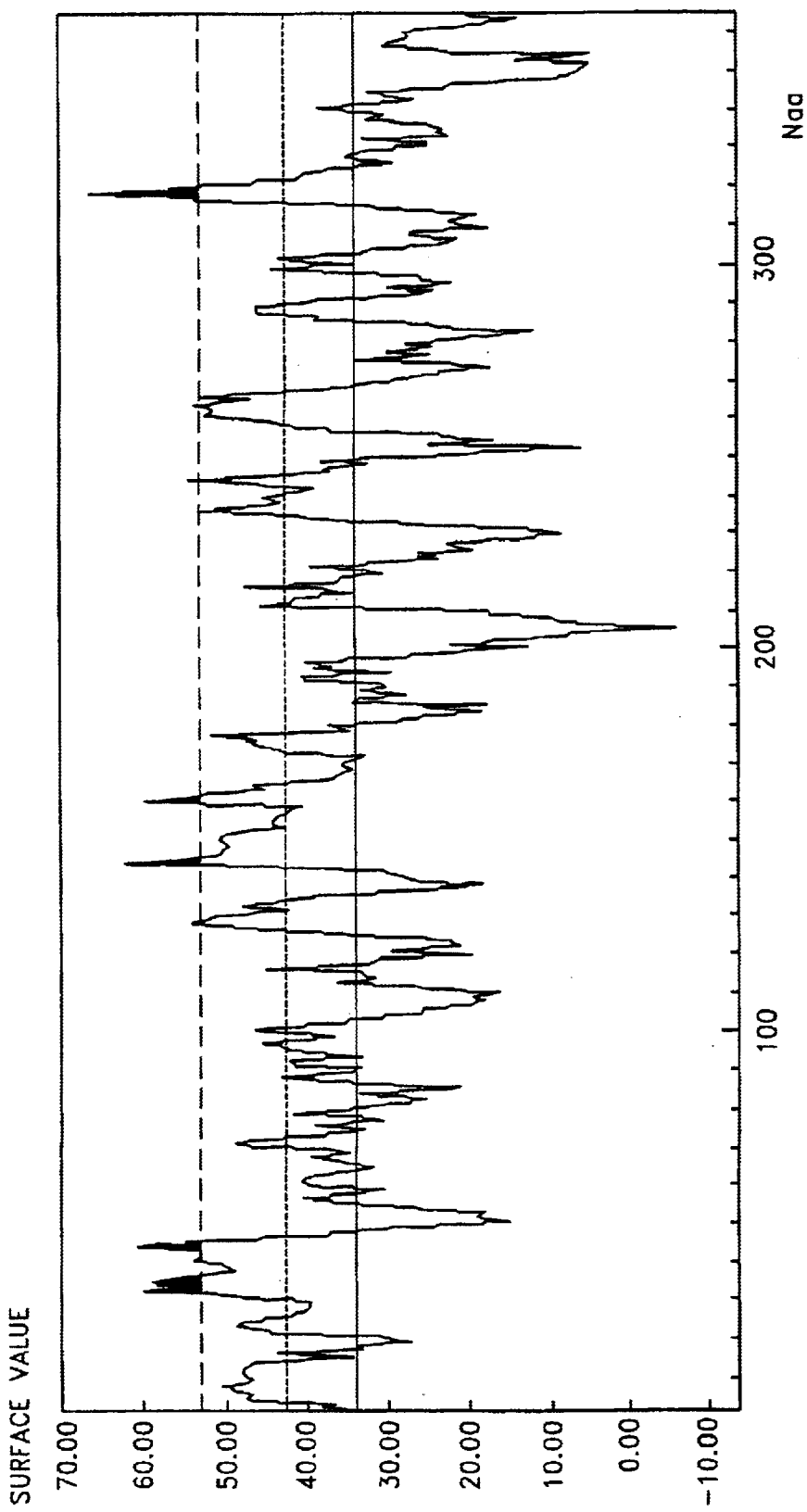
FIG. 2 depicts the hydrophilicity graph of the A3 sequence of factor VIII renumbered from 1 to 371 amino acids (surface value for each amino acid).
Figure 3:
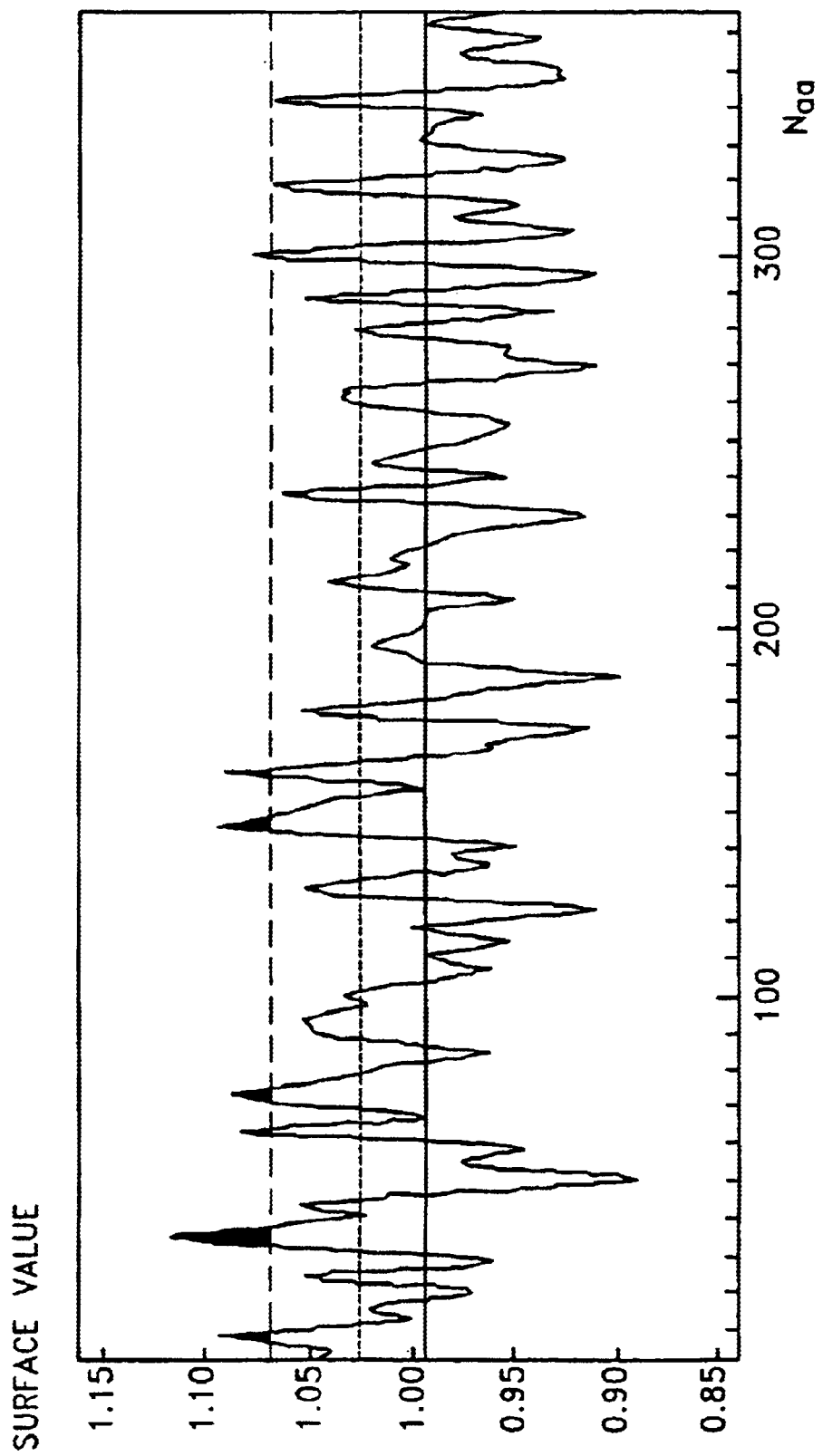
FIG. 3 depicts the flexibility graph for this A3 sequence of factor VIII.
Figure 4:
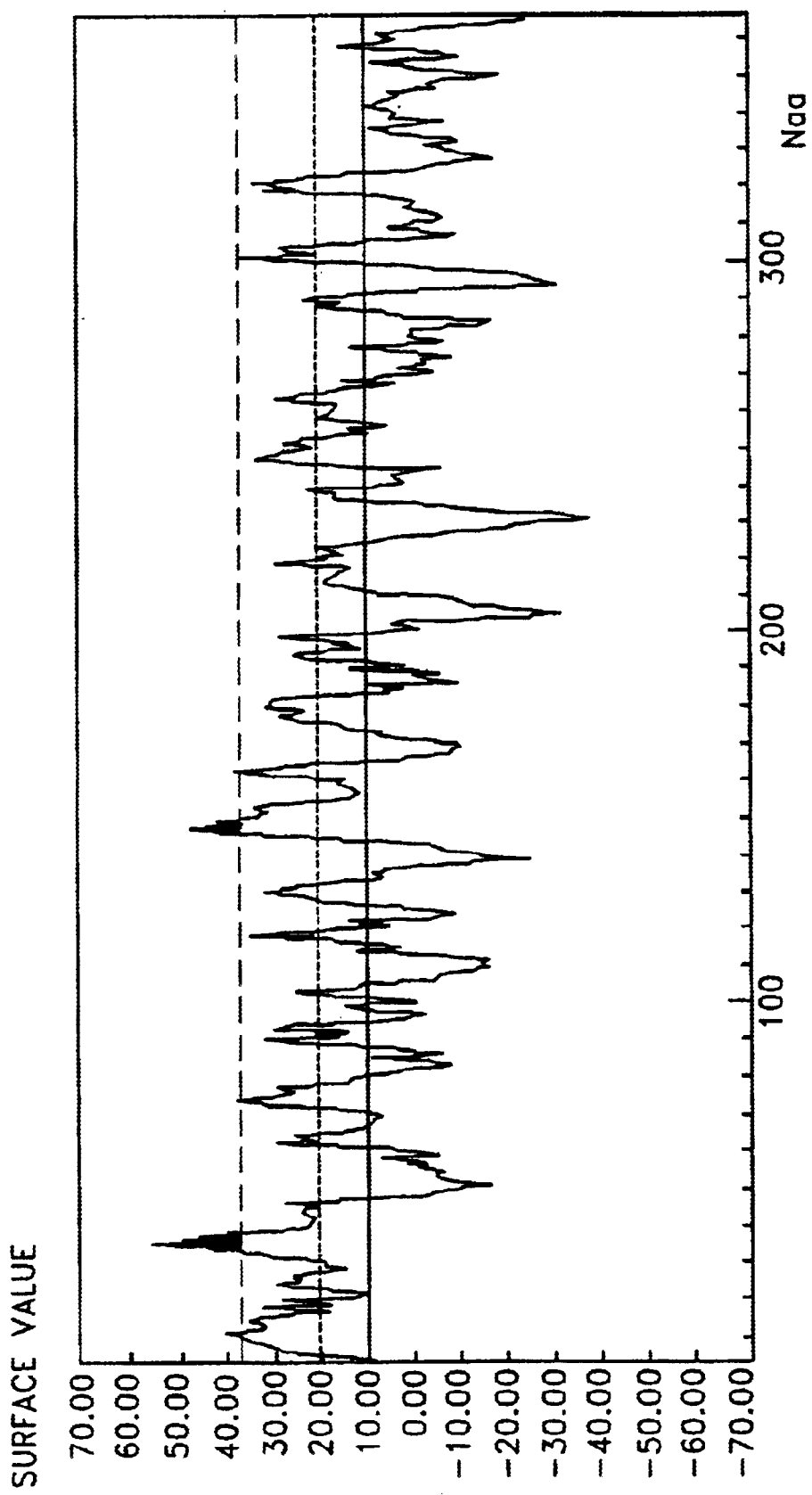
FIG. 4 depicts the accessibility graph for this A3 sequence of factor VIII.
Figure 5:
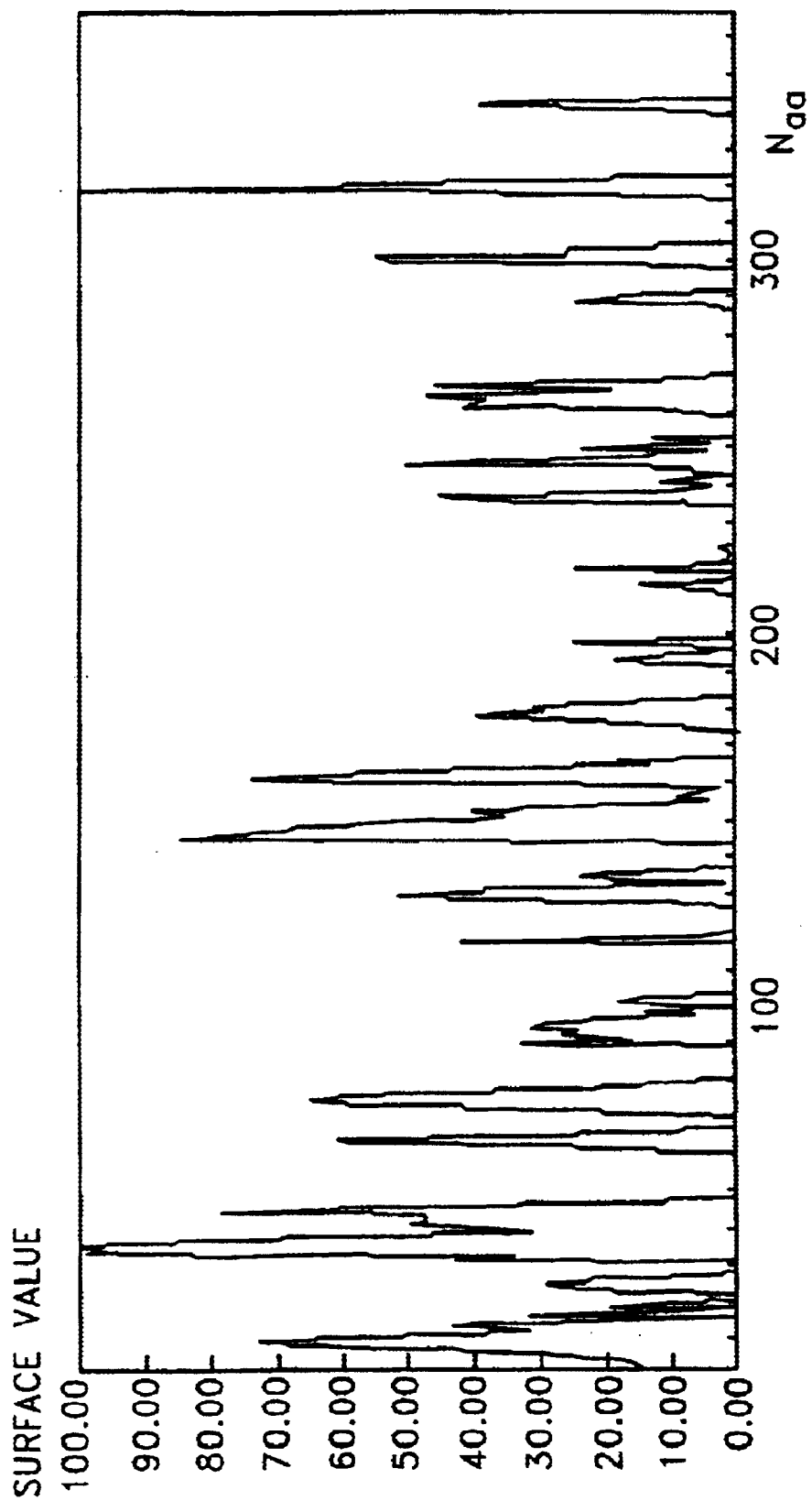
FIG. 5 depicts the general graph representing the sum of the values defined in Graphs 2 to 4.

The present invention relates to the antigenic polypeptide sequence of factor VIII and/or fragments of this sequence, as described by Verhar et al. (Nature, Vol. 312, p. 339 (1984)).

The "polypeptide sequence of factor VIII" is understood to be the natural human or animal sequence, which may be glycosylated and which has been obtained by purification from pools of plasma, in particular Cohn fraction I, by synthesis and/or by genetic manipulation (that is including a sequence from which portions which are not involved in the mechanism of blood coagulation may have been deleted) of factor VIII.

The present invention relates, in particular, to the antigenic polypeptide sequence of factor VIII which lacks fragments alanine 322-serine 750, leucine 1655-arginine 1689, lysine 1694-proline 1782 and aspartic acid 2170-tyrosine 2332.

The present invention relates, in particular, to the antigenic polypeptide sequences A1, A2, A3 and C (C1 and C2) of factor VIII.

In the remainder of the text, the amino acids will be represented by their three-letter abbreviations or by the single-letter symbol, as identified in the table below.

| Alanine | Ala | A | Leucine | Leu | L |
| Arginine | Arg | R | Lysine | Lys | K |
| Asparagine | Asn | N | Methionine | Met | M |
| Aspartic acid | Asp | D | Phenylalanine | Phe | F |
| Cysteine | Cys | C | Proline | Pro | P |
| Glutamine | Gln | Q | Serine | Ser | S |
| Glutamic acid | Glu | E | Threonine | Thr | T |
| Glycine | Gly | G | Tryptophan | Trp | W |

-continued

| Histidine | His | H | Tyrosine | Tyr | Y |
| Isoleucine | Ile | I | Valine | Val | V |

A first embodiment of the invention relates to the antigenic polypeptide sequence A3 of factor VIII, and to fragments and/or epitopes of this sequence. The said sequence is contained between glutamic acid 1649 and asparagine 2019, preferably between arginine 1652 and arginine 1917 or between arginine 1803 and arginine 1917, of the polypeptide sequence of factor VIII as published by Verhar et al. (Nature, vol. 312, p 339 (1984)) and Toole et al. (Nature, vol. 312, pp. 342–347 (1984)).

Preferably, the fragments of the said sequence are contained between arginine 1652 and arginine 1696, preferably between arginine 1652 and arginine 1689, between threonine 1739 and aspartic acid 1831 or between glutamic acid 1885 and arginine 1917.

The invention also relates to the sequence epitopes of these fragments, in particular:

the epitope contained between arginine 1652 and tyrosine 1664, defined by the following sequence:

```
Arg Thr Thr Leu Gln Ser Asp Gln Glu Glu Ile Asp Tyr   SEQ ID
1             5                       10              No:1:
``` the epitope contained between aspartic acid 1681 and arginine 1696, defined by the following sequence:

```
Asp Glu Asp Glu Asn Gln Ser Pro Arg Ser Phe Gln Lys Lys Thr Arg   SEQ ID
1             5                       10              15           No:2:
``` the epitope contained between threonine 1739 and tyrosine 1748, defined by the following sequence:

```
                                              SEQ ID No:3:
Thr Asp Gly Ser Phe Thr Gln Pro Leu Tyr
1             5                       10
``` the epitope contained between asparagine 1777 and phenylalanine 1785, defined by the following sequence:

```
Asn Gln Ala Ser Arg Pro Tyr Ser Phe   SEQ ID No:4:
1             5
``` the epitope contained between glutamic acid 1794 and tyrosine 1815, defined by the following sequence:

```
Glu Asp Gln Arg Gln Gly Ala Glu Pro Arg Lys Asn Phe Val Lys Pro   SEQ ID
1             5                       10              15           No:5:
Asn Glu Thr Lys Thr Tyr
              20
``` the epitope contained between methionine 1823 and aspartic acid 1831, defined by the following sequence:

```
Met Ala Pro Thr Lys Asp Glu Phe Asp   SEQ ID No:6:
1             5
``` the epitope contained between glutamic acid 1885 and phenylalanine 1891, defined by the following sequence:

```
Glu Thr Lys Ser Trp Tyr Phe   SEQ ID No:7:
1             5
``` the epitope contained between glutamic acid 1893 and alanine 1901, defined by the following sequence:

```
Glu Asn Met Glu Arg Asn Cys Arg Ala   SEQ ID No:8:
1             5
``` the epitope contained between aspartic acid 1909 and arginine 1917, defined by the following sequence:

```
Asp Pro Thr Phe Lys Glu Asn Tyr Arg   SEQ ID No:9:
1             5
```

Advantageously, the said sequence, its specific fragments and its epitopes exhibit an antigenic characteristic which is illustrated by appended FIGS. 2 to 5.

Another preferred embodiment of the invention relates to antigenic polypeptide sequence A1 of factor VIII and fragments and/or epitopes of this sequence.

Preferably, the fragments of the said sequence are contained between alanine 108 and methionine 355, preferably between alanine 108 and glutamine 228.

The invention also relates to the sequence epitopes of these fragments, in particular:

the epitope contained between alanine 108 and valine 128, defined by the following sequence:

```
Ala Ser Glu Gly Ala Glu Tyr Asp Asp Gln Thr Ser Gln Arg Glu Lys    SEQ ID No:10:
1               5                   10                  15
Glu Asp Asp Lys Val
            20
``` the epitope contained between glutamic acid 181 and leucine 192, defined by the following sequence:

```
                                        SEQ ID No:11:
Glu Gly Ser Leu Ala Lys Glu Lys Thr Gln Thr Leu
1               5                   10
``` the epitope contained between aspartic acid 203 and glutamine 218, defined by the following sequence:

```
Asp Glu Gly Lys Ser Trp His Ser Glu Thr Lys Asn Ser Leu Met Gln    SEQ ID No:12:
1               5                   10                  15
``` the epitope contained between aspartic acid 327 and methionine 355, defined by the following sequence:

```
Asp Ser Cys Pro Glu Glu Pro Gln Leu Arg Met Lys Asn Asn Glu Glu    SEQ ID No:13:
1               5                   10                  15
Ala Glu Asp Tyr Asp Asp Asp Leu Thr Asp Ser Glu Met
            20                  25
```

Another preferred embodiment of the invention relates to the antigenic polypeptide sequence A2 of factor VIII and fragments and/or epitopes of this sequence.

Preferably, the fragments of the said sequence are contained between aspartic acid 403 and aspartic acid 725, preferably between histidine 693 and aspartic acid 725.

The invention also relates to the sequence epitopes of these fragments, in particular:

the epitope contained between aspartic acid 403 and lysine 425, defined by the following sequence:

```
Asp Asp Arg Ser Tyr Lys Ser Gln Tyr Leu Asn Asn Gly Pro Gln Arg    SEQ ID No:14:
1               5                   10                  15
Ile Gly Arg Lys Tyr Lys Lys
                    20
``` the epitope contained between valine 517 and arginine 527, defined by the following sequence:

```
                                    SEQ ID No:15:
Val Glu Asp Gly Pro Thr Lys Ser Asp Pro Arg
1               5                   10
``` the epitope contained between histidine 693 and glycine 701, defined by the following sequence:

```
His Asn Ser Asp Phe Arg Asn Arg Gly    SEQ ID No:16:
1               5
``` the epitope contained between serine 710 and aspartic acid 725, defined by the following sequence:

```
Ser Cys Asp Lys Asn Thr Gly Asp Tyr Try Gly Asp Ser Tyr Glu Asp    SEQ ID No:17:
1               5                   10                  15
```

A final preferred embodiment of the invention relates to the antigenic polypeptide sequence C of factor VIII, and fragments and/or epitopes of this sequence. Preferably, the fragments of the said sequence are contained between lysine 2085 and lysine 2249, preferably between lysine 2085 and glycine 2121.

The invention also relates to the sequence epitopes of these fragments, in particular:

the epitope contained between lysine 2085 and phenylalanine 2093, defined by the following sequence:

```
Lys Thr Gln Gly Ala Arg Gln Lys Phe    SEQ ID No:18:
1                   5
``` the epitope contained between aspartic acid 2108 and glycine 2121, defined by the following sequence:

```
Asp Gly Lys Lys Trp Gln Thr Tyr Arg Gly Asn Ser Thr Gly    SEQ ID No:19:
1               5                   10
``` the epitope contained between glycine 2242 and lysine 2249, defined by the following sequence:

```
Gly Val Thr Thr Gln Gly Val Lys    SEQ ID No:20:
1                   5
```

The invention also relates to the major parts of the said epitopes or the said fragments, that is to say to the portions of the sequences of the said epitopes which contain the amino acids tyrosine and histidine, which unexpectedly display a particularly high affinity towards inhibitors of factor VIII. Preferably, these major parts contain the said amino acid tyrosine or histidine linked to at least two other identical or different amino acids.

These sequences, these fragments and these epitopes, in particular the major parts of the epitopes or the fragments, are particularly advantageously characterized by high hydrophilicity, such as described by Parker, Guo and Hodges (Biochemistry 25, pp 5425–5432 (1986)), considerable flexibility, such as described by Karplus and Schultz (Naturwissenschaften 72, p 212 (1985)) and considerable accessibility, such as described by Janin (Nature 277, pp 491–492 (1979)) (see FIGS. 2 to 5).

These fragments and these epitopes are, in particular, exposed on the surface of the factor VIII protein and exhibit a pronounced antigenic characteristic.

Advantageously, the said polypeptide sequence, its fragments, its epitopes and/or these major parts of the said fragments or the said epitopes are also independently immunogenic (that is to say they are immunogenic even without being complexed with a protein of large size such as BSA, haemocyanin, etc.), and preferably exhibit an immunoaffinity within inhibitors of factor VIII, such as anti-factor VIII antibodies, and/or exhibit an immunoaffinity for the receptors of the T lymphocytes and/or B lymphocytes.

This sequence, these fragments, these epitopes and/or the major parts of the said fragments or the said epitopes induce an immune reaction (antibody synthesis) when they are injected into a rabbit.

These characteristics are particularly pronounced in the case of the epitopes SEQ ID No: 2 and SEQ ID No: 5, which comprise sequences which are relatively "long" in amino acids, i.e. comprise 16 and 22 amino acids, respectively.

These sequences are therefore characterized by substantial immunogenicity towards monoclonal and polyclonal antibodies.

However, these sequences are sufficiently short to be readily obtained by synthesis.

As an example, peptides Asp 1681-Arg 1696 and Asp 327-Met 355 were synthesized in order to demonstrate the presence of anti-factor VIII antibodies in mouse sera using an ELISA test.

The free peptides (not coupled to a carrier protein) were injected into two BALB/C mice in accordance with the following protocol:

day 0 100 µg of peptide emulsified in incomplete Freund's adjuvant are injected intramuscularly.

days 7, 14, 21 and 28: immunization with 50 µg of peptide.

Figure 6:
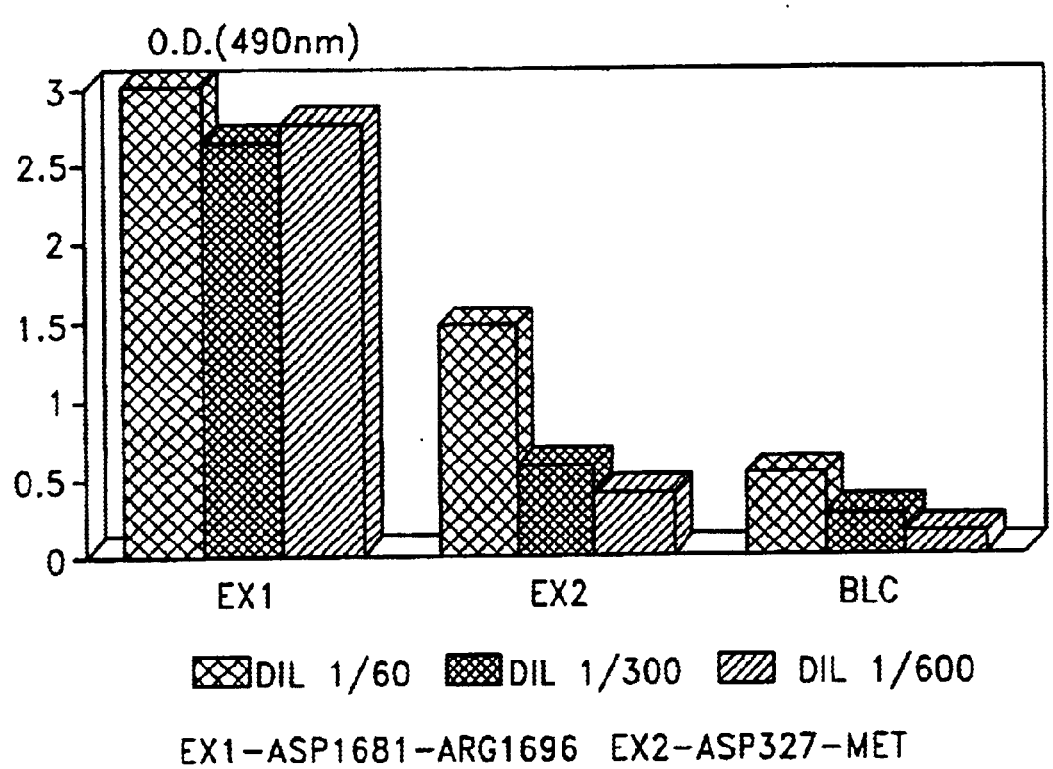
FIG. 6 depicts the demonstration of anti-factor VIII antibodies in mouse sera using an ELISA test.

A sample of blood is withdrawn on each day before the injection. Polystyrene microtitration plates (NUNC) are saturated with a preparation of plasma factor which is diluted with the aid of 40 IU/ml. 50 µl volumes of increasing dilutions (1/60, 1/300 and 1/600) of mouse antisera are added to the wells. Following incubation and washing, the presence of anti-factor VIII antibodies is demonstrated by adding 50 µl of a 1/5000 dilution of a rabbit anti-mouse IgG antibody which is labelled with biotin. Following incubation and washing, the wells are incubated with 50 µl of avidin/peroxidase (1/2500) and washed, with 100 µl of OPD finally being added to the wells. The optical density is measured at 490 nm. The results of the ELISA are presented in appended FIG. 6 (EX1, EX2 and a sample, termed BLC, which serves as the blank).

The present invention also relates to the conformational epitopes which comprise at least two different fragments of the said sequence, at least two sequence epitopes and/or at least two major parts of the said epitopes or the said different fragments according to the invention and identified above.

The conformational epitopes are made up of two or more different portions of a polypeptide sequence, which portions are located in proximity to each other when the protein is folded in its tertiary or quaternary structure.

These epitopes are capable of being "recognized" (that is to say of exhibiting an immunoaffinity), preferably simultaneously, with inhibitors of factor VIII, in particular B lymphocytes (by way of the major histocompatibility locus (MHC I and/or II)) and/or anti-factor VIII antibodies (Scandella et al., Blood 76, p 437 (1990)).

Preferably, the said sequence, the said fragments, the said epitopes and/or the major parts of the said epitopes or the said fragments are complexed with a carrier protein or a carrier peptide, such as BSA or haemocyanin, in such a way as to form a complex exhibiting a more powerful immunogenicity.

Another aspect of the present invention relates to an inhibitor of factor VIII which exhibits an immunoaffinity with the antigenic polypeptide sequence according to the present invention, with fragments and epitopes of this sequence, with major parts of the said epitopes or the said fragments and/or with the complex according to the invention.

An inhibitor is understood to mean any biological molecule or cell which intervenes with and/or against factor VIII and is capable of giving rise to immune disorders.

In particular, such an inhibitor can be an anti-factor VIII monoclonal or polyclonal antibody (gamma-globulin) or antibody fragment (such as the hypervariable Fab portion of the said antibody) which inactivates the said factor VIII and/or which inhibits the binding of factor VIII to the von Willebrand factor and/or to membrane phospholipids.

Advantageously, the said inhibitors are synthesized by a "chimaeric" animal which comprises a human immune system, such as an hu-SCID mouse producing human antibodies.

SCID (severe combined immunodeficient) mice are mice which exhibit a deficiency in functional B and T lymphocytes due to dysfunction of the recombination of the genes which are responsible for the antigenic receptors. The immune system of the SCID mice can be reconstituted using immunocompetent cells of human origin which are derived from foetal organs or peripheral blood (Mosler et al. (1988)).

Once reconstituted, these hu-SCID mice produce human antibodies either spontaneously or after immunization.

There does not appear to be any dramatic cross reactivity between human factor VIII and murine factor VIII (Kessler, 1991).

The peripheral blood lymphocytes are taken from several types of donor: non-haemophilic volunteers, haemophilics who lack inhibitors which can be detected by standard methods, haemophilics who exhibit substantial inhibitor levels and donors who are producing autoantibodies.

This model is employed in two types of study. Firstly, the mice are reconstituted with cells from a single donor, and it is possible to compare the antigenicity of several factor VIII preparations once the reproducibility of the system has been verified.

On the other hand, it is possible, using this model, to obtain and study an anti-factor VIII response at the clonal level.

Study of the specific monoclonal response of the B cells is very important since this enables the sequential and conformational epitopes of factor VIII to be identified precisely. The B cells are cultured, cloned in the presence or absence of anti-CD40 antibodies, from the spleens of mice which are producing anti-factor VIII antibodies, or else transformed in the presence of EBV virus. The anti-CD40 antibodies recognize a membrane antigen and activate the B cells in the presence of a fibroblast line (Banchereau et al. 1991)). It is consequently possible to envisage using these immunodominant epitopes as a possible target for immunotherapy.

Determination of the MHC class I and class II markers which are carried by the B lymphocyte clones makes it possible to analyze the immune response of the anti-factor VIII antibodies at the genetic level and thereby to follow recognition by the specific T cells. This is also an excellent method for seeing whether there is a risk factor associated with this pathology.

The BALB/C mice which are selected for preparing the anti-factor VIII Mabs are firstly injected on three occasions, at 2 week intervals, with a solution of recombinant factor VIII (rFVIII). This type of preparation has the advantage of containing a high-purity factor VIII at elevated concentration together with a minimum of contaminating proteins. Four days after the last injection, the splenocytes are fused with the cells from a mouse myeloma (SP207) (van Snick and Coulie (1982)). The hybridomas which are producing anti-factor VIII antibodies are selected by the ELISA technique, using polystyrene plates on which rFVIII has previously been insolubilized. The hybridoma supernatants containing the anti-factor VIII antibodies are cloned by the limiting dilution technique and then cultured in vitro.

The antibodies are purified from these supernatants by means of chromatography.

The ELISA technique is used to quantify, and to determine the light chain (k or 1) and the subclass (IgG1, IgG2a, IgG2b or IgG3) of the anti-factor VIII Mabs.

The epitopes which are recognized on the factor VIII molecule are determined by means of the immunotransfer technique using solutions of native factor VIII or factor VIII which has been cleaved enzymically with thrombin.

The ability of each of the anti-factor VIII Mabs which have been produced to inhibit function is evaluated both by a coagulation method (Bethesda method) (Kasper et al. (1975)) and by a chromogenic method which is based on the ability which is possessed by factor X, which has been activated by association with factor VIII and activated factor IX, to transform a colourless substrate into a coloured substrate (Svendsen et al. (1984)).

The cell lines which produce human monoclonal anti-factor VIII antibodies are derived from human B lymphocytes which are taken from the abdominal cavity of SCID mice which have been immunized with different batches of factor VIII after reconstitution of the immune system of the animals with human lymphocytes. The B lymphocytes are cultured in the presence of fibroblast cells which express a receptor for the immunoglobulin Fc moiety, to which is attached a monoclonal anti-CD40 antibody. These cells, which have been activated by polymerization of the CD40 receptor, are then infected and immortalized with Epstein-Barr virus (Kozbor, (1981)). The cell lines which produce the sought-after antibodies can then be subcloned.

Another aspect of the invention relates to an anti-inhibitor which is characterized in that it is directed against the said previously described factor VIII inhibitor.

An anti-inhibitor which is directed against the factor VIII inhibitor is understood to mean any biological molecule and/or cell which is capable of interfering with the said inhibitor in such a way as to ensure its inactivation.

Preferably, such an anti-inhibitor is an anti-anti-factor VIII idiotype (monoclonal or polyclonal) antibody or antibody fragment.

Advantageously, these anti-inhibitors which are directed against the factor VIII inhibitors are synthesized by a "chimaeric" animal exhibiting a human immune system, such as an hu-SCID mouse.

Only mice which produce less than 10 $\mu$g/ml residual immunoglobulins are used for the experiments.

The model is developed using peripheral leucocytes which are derived from volunteers who have been immunized against tetanus.

The reconstitution is effected by means of a single i.p. injection of from 15 to $20.10^6$ mononuclear cells of human origin. These cells are obtained after centrifuging peripheral blood (approximately 200 ml) on a Ficoll/Hypaque gradient. From twelve to twenty mice can be reconstituted from one single donor. The production of human immunoglobulins is measured as a function of time.

The anti-anti-factor VIII idiotype antibodies are purified from a pool of starting plasma which is assembled from voluntary donations from at least 7200 donors in order to increase the probability of finding anti-idiotype antibodies by means of immunoaffinity using human anti-factor VIII antibodies which are covalently attached to a Sepharose column or attached by means of an Fc moiety to a protein G column. Following fractionation, by means of the Cohn-Oncley method, two IgG-rich fractions, Fr II and Fr III, are obtained. They will serve as the starting preparation for purifying the anti-idiotype antibodies. These monoclonal antibodies will be obtained from B cells which have been taken from haemophilic patients. These cells have initially proliferated in SCID mice and have been transformed into secretory cell cultures by the EBV virus. Use of these human monoclonal antibodies makes it possible to avoid introducing non-human proteins into the therapeutic preparations. These preparations are evaluated, by means of detailed immunochemical analysis, for their efficiency in neutralizing the inhibitors which are derived from the largest possible number of haemophilic patients. Several physical (treatment with UVCF radiation), thermal and/or chemical (for example using a solvent/detergent) viral inactivation steps are introduced into the purification process in order to ensure the greatest possible degree of viral safety.

The idiotype which is peculiar to the human antibodies is analyzed by sequencing the variable moiety of the molecule. These data are of the utmost importance because they are of great value both in diagnosing and regulating the production of anti-factor VIII antibodies.

Up to the present time, the source of the antibodies which are required for preparing antigen/antibody complexes has been autologous, that is to say the patient himself was supplying the antibodies. It has recently become clear that normal individuals, having normal levels of circulating factor VIII, produce anti-factor VIII antibodies whose activity in the plasma is limited by corresponding anti-idiotype antibodies. Anti-factor VIII antibodies which have been prepared from a gammaglobulin pool can advantageously replace the autologous source.

It is also possible to obtain human B cells which have been transformed with the EBV virus and which produce inhibitors from haemophilic or non-haemophilic patients. Four lines have thus been obtained, with one of these lines recognizing the light chain of factor VIII. SCID mice have been repopulated with inhibitor-secreting B cells derived from haemophilic or non-haemophilic patients. Production is stimulated by injecting plasma factor VIII and recombinant factor VIII. It is therefore possible to obtain continuous in-vitro cultures which are producing the said inhibitors. Anti-anti-factor VIII idiotype antibodies can also be produced continuously using this technique.

Another aspect of the invention relates to a pharmaceutical composition which comprises an element which is selected from the group consisting of the said antigenic polypeptide sequence of factor VIII, fragments and epitopes of this sequence and/or major parts of the said epitopes or the said fragments, an inhibitor of factor VIII which is directed against them, an anti-inhibitor which is directed against the said inhibitor, and/or a mixture of these.

Another aspect of the invention relates to a diagnostic and/or purification device such as a diagnostic kit or a chromatography column (such as described by Ezzedine et al. (1993)), which comprises an element which is selected from the group consisting of the antigenic polypeptide sequence according to the invention, fragments and epitopes of this sequence and/or the major parts of the said epitopes or the said fragments, the complex according to the invention, an inhibitor which is directed against them, an anti-inhibitor which is directed against the said inhibitor, and/or a mixture of these.

The purification device can therefore consist of a chromatography column such as described by Ezzedine et al. (1993) which comprises the sequence of factor VIII, fragments and epitopes of this sequence and/or the major parts of the said fragments or epitopes, which are attached to the solid phase of the chromatography column.

A physiological liquid (such as serum), which is derived from a patient and which comprises inhibitors of factor VIII, is then caused to pass through this chromatography column, with the said inhibitors (for example antibodies) becoming attached specifically to the said factor VIII, the said fragments, the said epitopes or the said major parts.

Following elution, it is possible to collect the said inhibitors by causing them to react with anti-inhibitors (anti-anti-factor VIII idiotype antibodies).

It is also possible to characterize the anti-anti-factor VIII idiotype antibodies which are present in a serum by causing these anti-inhibitors to be passed through a chromatography column on which inhibitors of factor VIII have been attached to the solid phase.

A final aspect of the invention relates to the use of the pharmaceutical composition according to the invention for preparing a medicament to be used for preventing and/or treating immune disorders, in particular those which are induced by inhibitors of factor VIII, inhibitors of the binding of factor VIII and the von Willebrand factor (vWF) and/or inhibitors of the binding of factor VIII to membrane phospholipids.

References.

Aledort, L. M. (1993), Sem Hematol 30, 7–9
Bardelle, C., Furie, B., Furie, B. C. and Gilbert, G. E. (1993), J. Biol. Chem. 268, 8815–8824
Barrowcliffe, T. W. (1993), Sem Thromb Hemost 19, 73–79
Bennet, B., Ratnoff, O. D. (1972), Procédé Sol Exp Biol Med 143, 137–155
Bihoreau, N. (1992), MIS 8, 1043–1050
Blomm, A. L. (1992), Haemost 22, 268–275
Blanchereau, J., de Paoli, P., Vallé, A., Garcia, E. and Rousset, F. (1991), Science 251, 70
Cauldfield, M. J. and Schaffer, D. (1987), J. Immunol 138, 3680
Ciavarella, N. and Shiavoni, M. (1992), Lancet 339, 1301
Clyne, L. P., Levy, A., Stein and McPhedran, P. (1992), Thromb and Haemost 68, 475–476
Dietrich, G., Algiman, M., Sultan, Y., Nydegger, U. E., Kazatchkine, M. D. (1992), Blood 79, 2946–2951
Ehrenforth, S., Kreuz, W., Scharrer, I., Linde, R., Funk, M., Gungor, T., Krackhardt, B. and Kornhuber, B. (1992), Lancet 339, 594–598
Elder, B., Lakich, D. and Gitschier, J. (1993), Genomics 16, 374–379
Ewing, N. P., Sanders, N. L., Dietrich, S. L. and Kasper, C. K. (1988), JAMA 259, 65–68
Fay, P. J. (1993), Thromb Haemost 70, 63–67
Fulcher, C. A., Roberts, I. Z., Holland, Tous and Zimmerman, Tous (1985), J. Clin Invest 76, 1117–1124
Foster, P. A., Fulcher, C. A., Houghten, R. A. and Zimmerman, T. S. (1985), Blood 75, 1999–2004
Gilles, J. G., Armout, J. Vermylen, J and Saint-Rémy, J. M. (1991), XIVth Int Congress Allerg and Clin Immunol October 13–18
Gilles, J. G. and Saint-Rémy, J. M. (1993a), XIVth Congress Int Soc Thromb Haemost July 49
Gomperts, E. D., de Biasi, R. and De Vreker, R. (1992), Transfusion Med Rev 1, 44–54
Gruppo, R. (1991), Thromb Haemostas 65, 1168
Halter, R., Carnwath, J., Espanon, G., Herrman, D., Lemme, E., Niemenn, H. and Paul, D. (1993), Theriogenology 39, 137–149
Hay, C. R. M. and Bolton-Maggs (1991), Transfusion Med Rev V, 145–151
Hedner, U. and Tenborn (1985), Thromb Haemostas 54, 776–779
Hultin, M. B. (1991), Am J. Med. 91 (Suppl 5A), 23–27
Hoyer, L. W. (1991), Am J. Med. 91 (Suppl 5A), 405–409
Ingerslev, J., Feldstedt, M. and Sindet-Pedersen (1991), Lancet 338, 831–832
Kalafatis, M., Rand, M. D., Jenny, R. J., Erlich, Y. H. and Mann, K. G. (1993), Blood 81, 704–709
Kaufman, R j. (1992), Transfusion Med Rev VI, 235–246
Kasper, C. K., Aledort, L. M., Edson, J. R., Fratantone, J., Green, D. et al. (1975), Thrombos Diathes Haemorh 34, 869

Kemball-Cook, G. and Barrowcliffe, T. W. (1992), Thromb Res 67, 57–71
Kessler, C. M. (1991), Am. J. Med. 91 (Suppl. 5A), 15–19
Kosbor, D. and Roder, J. C. (1981), 127–1275
Leroy, B. L., Lachapelle, J. M., Jacquemin, M. G. and Saint-Rémy, J. M. R. (1992), Dermatology 184:271
Leyte et al. (1989), Biochem J. 263, 189–194
Lian, E. C. Y., Larcada, A. F. and Chiu, A. Z. Y. (1989), Ann Int Med 110, 771–778
Ljung, R., Petrini, P., Lindgren, A. C., Tengborn, L. and Nilsson, I. M. (1992), Lancet 339, 1550
Lorenzo, J. L., Garcia, R. and Molina, R. (1992), Lancet 339, 1551
Lottenburg, R. Kentro, T. B. and Kitchins, C. S. (1987), 147, 1077–1081
Lozier, J. N., Santagostino, E., Kasper, C k., Teitel, J. M. and Hay, C. R. M. (1993), Sem Hematol 30, 10–21
Madhok, R., Smith, J., Jenkind, A. and Lowe, G. D. O. (1991), Br. J. Haematol 79, 235–238
Mc Cune, L. M., Namikawe, R., Kaneshima, H., Schultz, L. D., Lieberman, M. and Weissman, I. L. (1988), Sciences 241, 1632–1639
Moreau, P. H., Staikowsky, F., Laneelle, D., Dellile, F., Simonin, D., Schiffer, C. and Laurian, Y. (1993), Presse Méd 22, 472–479
Mosler, D. E., Gulizia, R. J., Baird, S. B. and Wilson, D. B. (1988), Nature 335, 256–259
Nesheim, M. E. Furmaniak-Kazmierczak, E., Henin, C. H. and Côté, G. (1993), Thromb and Haemost 70, 80–86
Nilsson, J. M., Berntop, E., Zettervall, O. and Dahlbäck, B. (1990), Blood 10, 378–383
Peerlinck, K., Arnout, J., Tamise, A., Vanherle, P., Fondu, P. and Vermylen, J. (1991), Acta Clin Belg 46, 298–304
Peerlinck, K., Arnout, J., Gilles, J. G., Saint-Rémy, J. M. and Vermylen, J. (1993a), Thromb Haemost 69, 2, 115–118
Peerlinck, K., Rosendaal, F. R. and Vermylen, J. (1993a), Blood 81, 3332–3335
Scandella, D., de Graaf Mahoney, S., Mattingly, M., Roeder, D., Timmons, L. and Fulcher, C. A. (1985), Proc. Natl. Acad. Sci. USA 85, 6152–6156
Scandella, D., Timmons, L., Mattingly, M., Trabold, N. and Hoyer, L. W. (1992), Thromb Haemost 65, 1160
Seremitis, S., Aledort, L., Lusher, M., Hilgartner, M., Mannucci, P. M. and Mariani, G. (1991), Thromb Haemostas 65, 1160
Smith, C. I. E., Habedi, M., Islam, K. B., Johansson, M. E. B., Christenson, B. and Hammerström, L. (1991), Immunol Rev 124, 113–135
Sultan, Y., Rossi, F. and Kazatchkine, M. (1987), Proc. Natl. Acad. Sci. 84, 828–831
Sultan, Y., White, G. C., Aronstam, A., Bosser, C., Brackmann, H. H. et al. (1986), Nouv Rev Fr Hematol 28, 85–89
Sultan, Y. and French Hemophilia Study Group (1992), Thromb Haemost 67, 600–602
Svendsen, L., Brogli, M., Lindeberg, G. and Stocker, K. (1984), Thrombos Res 34, 457
Triulzi, D. J., Heal, J. M. and Blumberg, N. (1990), In "Transfusion Medicine in the 1990s", Ed. Nance, S. T.; American Association of Blood Banks; Arlington, Va.
Van Snick, J. and Coulie, P. (1982), J. Exp Med 155, 219
Vermylen, J. and Peerlinck, K. (1991), Acta Clin Belg 46, 419–420
Wadhwa, M., Dilger, P., Tubbs, J., Barrowcliffe, T., Mahon, B. and Thorpe, R. (1992), Br. J. Haematol 82, 578–583
Ware, J., MacDonald, M. J., Lo, M., de Graaf, S. and Fulcher, C. A. (1992), Blood Coagul Fibrin 3, 703–716
Webb, E., Tkalcevic, S., Hocking, D. and Nisbet, I. (1993), Biochem Biophys Res Commun 190, 536–543

What is claimed is:

1. An isolated antigenic fragment of the human Factor VIII polypeptide of SEQ ID NO: 21, said fragment comprising at least 7 amino acids of a human Factor VIII fragment selected from the group consisting of a human Factor VIII fragment extending from arginine 1652 to arginine 1696 inclusive, a human Factor VIII fragment extending from threomine 1739 to tyrosine 1748 inclusive (SEQ ID NO: 3), a human Factor VIII fragment extending from asparagine 1777 to phenylalanine 1785 inclusive (SEQ ID NO: 4), a and a human Factor VIII fragment extending from glutamic acid 1885 to arginine 1917 inclusive.

2. The isolated antigenic fragment according to claim 1, wherein said human Factor VIII fragment comprises an epitope selected from the up consisting of: a human Factor VIII fragment extending from arginine 1652 to tyrosine 1664 (SEQ ID No: 1), a human Factor VIII fragment extending from threonine 1739 to tyrosine 1748 (SEQ ID No: 3), a human Factor VIII fragment extending from asparagine 1777 to phenylalanine 1785 (SEQ ID No: 4), a human Factor VIII fragment extending from glutamic acid 1885 to phenylalanine 1891 (SEQ ID No: 7), a human Factor VIII fragment extending from glutamic acid 1893 to alanine 1901 (SEQ ID No: 8), and a human Factor VIII fragment extending from aspartic acid 1909 to arginine 1917 (SEQ ID No: 9).

3. The isolated antigenic fragment according to claim 1, wherein said antigenic polypeptide comprises tyrosine or histidine.

4. An isolated conformational epitope comprising at least two different human Factor VIII fragments of claim 2, wherein said fragments are positioned in proximity to each other when the protein is folded in its tertiary or quaternary structure to form a conformational epitope which is recognized by an inhibitor of Factor VIII selected from the group consisting of B lymphocytes, MHC I proteins, MHC II proteins, and anti-Factor VIII antibodies.

5. An isolated conformational epitope comprising at least two different epitopes from a fragment of the human Factor VIII polypeptide of SEQ ID NO: 21 wherein said fragment is selected from the group consisting of a human Factor VIII fragment extending from arginine 1652 to arginine 1696 inclusive, a human Factor VIII fragment extending from threonine 1739 to aspartic acid 1831, inclusive, and a human Factor VIII fragment extending from glutamic acid 1885 to arginine 1917 inclusive.

6. A complex, comprising a carrier protein or a carrier peptide linked to the fragment of claim 1 or the conformational epitope of claim 5, wherein said complex has higher immunogenicity than said polypeptide of claim 1.

7. A pharmaceutical composition comprising at least the antigenic fragment of claim 1, or the conformational epitope of claim 5 and an acceptable pharmaceutical vehicle.

8. The complex of claim 6, wherein said carrier protein or said carrier peptide are bovine serum albumin or hemocyanin.

9. An isolated polypeptide, consisting of a fragment of the human Factor VIII polypeptide of SEQ ID NO: 21, wherein said fragment is selected from the group consisting of a human Factor VIII fragment between arginine 1652 and arginine 1696 inclusive, a human Factor VIII fragment between glutamic acid 1885 and arginine 1917 inclusive, and a fragment comprising at least 7 amino acids thereof, wherein said polypeptide is antigenic.

10. A pharmaceutical composition, comprising the antigenic polypeptide of claim 9 and an acceptable pharmaceutical vehicle.

11. A complex, comprising a carrier protein or a carrier peptide linked to the antigenic polypeptide of claim 9, wherein said complex has higher immunogenicity than said polypeptide of claim 9.

12. The complex of claim 11, wherein said carrier protein or said carrier peptide are bovine serum albumin or hemocyanin.

13. A conformational epitope comprising at least two different human Factor VIII fragments of claim 9, wherein said fragments are positioned in proximity to each other when the protein is folded in its tertiary or quaternary structure to form a conformational epitope which is recognized by an inhibitor of Factor VIII selected from the group consisting of B lymphocytes, MHC I proteins, MHC II proteins, and anti-Factor VIII antibodies.

14. An isolated polypeptide, consisting of a fragment of the human Factor VIII polypeptide of SEQ ID NO: 21, wherein said human Factor VIII fragment consists of an epitope selected from the group consisting of: a human Factor VIII fragment contained between arginine 1652 and tyrosine 1664 (SEQ ID No: 1), a human Factor VIII fragment contained between threonine 1739 and tyrosine 1748 (SEQ ID No: 3), a human Factor VIII fragment contained between asparagine 1777 and phenylalanine 1785 (SEQ ID No: 4), a human Factor VIII fragment contained between glutamic acid 1794 and tyrosine 1815 (SEQ ID No: 5), a human Factor VIII fragment contained between methionine 1823 and aspartic acid 1831 (SEQ ID No: 6), a human Factor VIII fragment contained between glutamic acid 1885 and phenylalanine 1891 (SEQ ID No: 7), a human Factor VIII fragment contained between glutamic acid 1893 and alanine 1901 (SEQ ID No: 8), and a human Factor VIII fragment contained between aspartic acid 1909 and arginine 1917 (SEQ ID No: 9), wherein said polypeptide is antigenic.

15. A pharmaceutical composition, comprising the antigenic polypeptide of claim 14 and an acceptable pharmaceutical vehicle.

16. A complex, comprising a carrier protein or a carrier peptide linked to the antigenic polypeptide of claim 14, wherein said complex has higher immunogenicity than said polypeptide of claim 9.

17. The complex of claim 16, wherein said carrier protein or said carrier peptide are bovine serum albumin or hemocyanin.

18. A conformational epitope comprising at least two different human Factor VIII fragments of claim 14, wherein said fragments are positioned in proximity to each other when the protein is folded in its tertiary or quaternary structure to form a conformational epitope which is recognized by an inhibitor of Factor VIII selected from the group consisting of B lymphocytes, MHC I proteins, MHC II proteins, and anti-Factor VIII antibodies.

19. An isolated polypeptide, consisting of a fragment of the human Factor VIII polypeptide of SEQ ID NO: 21, wherein said fragment is threonine 1739 to aspartic acid 1831, wherein said polypeptide is antigenic.

* * * * *

UNITED STATES PATENT AND TRADEMARK OFFICE
CERTIFICATE OF CORRECTION

PATENT NO. : 6,866,848 B2
DATED : March 15, 2005
INVENTOR(S) : Laub et al.

It is certified that error appears in the above-identified patent and that said Letters Patent is hereby corrected as shown below:

Column 37,
Line 46, please delete "threomine" and insert therefore -- threonine --.

Signed and Sealed this

First Day of November, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,866,848 B2 | Page 1 of 1 |
| APPLICATION NO. | : 08/765837 | |
| DATED | : March 15, 2005 | |
| INVENTOR(S) | : Laub et al. | |

It is certified that error appears in the above-identified patent and that said Letters Patent is hereby corrected as shown below:

On the title page, item [54] and column 1, line 5:
    In the title, delete "POLYPETIDE" and insert therefor --POLYPEPTIDE--.

On the cover page, line (86) designating the PCT No., please delete

"PCT/BE95/00063" and insert therefor --PCT/BE95/0068--.

Signed and Sealed this

Fifth Day of September, 2006

JON W. DUDAS
*Director of the United States Patent and Trademark Office*

```
SEQUENCE LISTING

<160> NUMBER OF SEQ ID NOS: 21

<210> SEQ ID NO 1
<211> LENGTH: 13
<212> TYPE: PRT
<213> ORGANISM: Homo sapiens
<220> FEATURE:
<221> NAME/KEY: DOMAIN
<222> LOCATION: (1)...(13)
<223> OTHER INFORMATION: Fragment of Human Factor VIII Protein from Arg
      1652 through Tyr 1664

<400> SEQUENCE: 1

Arg Thr Thr Leu Gln Ser Asp Gln Glu Glu Ile Asp Tyr
1               5                   10

<210> SEQ ID NO 2
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: Fragment of Human Factor VIII Protein from Asp
      1681 through Arg 1696

<400> SEQUENCE: 2

Asp Glu Asp Glu Asn Gln Ser Pro Arg Ser Phe Gln Lys Lys Thr Arg
```

-continued

```
<210> SEQ ID NO 3
<211> LENGTH: 10
<212> TYPE: PRT
<213> ORGANISM: Homo sapiens
<220> FEATURE:
<221> NAME/KEY: DOMAIN
<222> LOCATION: (1)...(10)
<223> OTHER INFORMATION: Fragment of Human Factor VIII Protein from Thr
      1739 through Tyr 1748

<400> SEQUENCE: 3

Thr Asp Gly Ser Phe Thr Gln Pro Leu Tyr
1               5                   10

<210> SEQ ID NO 4
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: Fragment of Human Factor VIII Protein from Asn
      1777 through Phe 1785

<400> SEQUENCE: 4

Asn Gln Ala Ser Arg Pro Tyr Ser Phe
1               5

<210> SEQ ID NO 5
<211> LENGTH: 22
<212> TYPE: PRT
<213> ORGANISM: Homo sapiens
<220> FEATURE:
<221> NAME/KEY: DOMAIN
<222> LOCATION: (1)...(22)
<223> OTHER INFORMATION: Fragment of Human Factor VIII Protein from Glu
      1794 through Tyr 1815

<400> SEQUENCE: 5

Glu Asp Gln Arg Gln Gly Ala Glu Pro Arg Lys Asn Phe Val Lys Pro
1               5                   10                  15

Asn Glu Thr Lys Thr Tyr
            20

<210> SEQ ID NO 6
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: Fragment of Human Factor VIII Protein from Met
      1823 through Asp 1831

<400> SEQUENCE: 6

Met Ala Pro Thr Lys Asp Glu Phe Asp
1               5

<210> SEQ ID NO 7
<211> LENGTH: 7
<212> TYPE: PRT
<213> ORGANISM: Homo sapiens
<220> FEATURE:
<221> NAME/KEY: DOMAIN
<222> LOCATION: (1)...(7)
<223> OTHER INFORMATION: Fragment of Human Factor VIII Protein from Glu
      1885 through Phe 1891
```

```
<400> SEQUENCE: 7

Glu Thr Lys Ser Trp Tyr Phe
1               5

<210> SEQ ID NO 8
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: Fragment of Human Factor VIII Protein from Glu
      1893 through Ala 1901

<400> SEQUENCE: 8

Glu Asn Met Glu Arg Asn Cys Arg Ala
1               5

<210> SEQ ID NO 9
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: Fragment of Human Factor VIII Protein from Asp
      1909 through Arg 1917

<400> SEQUENCE: 9

Asp Pro Thr Phe Lys Glu Asn Tyr Arg
1               5

<210> SEQ ID NO 10
<211> LENGTH: 21
<212> TYPE: PRT
<213> ORGANISM: Homo sapiens
<220> FEATURE:
<221> NAME/KEY: DOMAIN
<222> LOCATION: (1)...(21)
<223> OTHER INFORMATION: Fragment of Human Factor VIII Protein from Ala
      108 through Val 128

<400> SEQUENCE: 10

Ala Ser Glu Gly Ala Glu Tyr Asp Asp Gln Thr Ser Gln Arg Glu Lys
1               5                   10                  15

Glu Asp Asp Lys Val
            20

<210> SEQ ID NO 11
<211> LENGTH: 12
<212> TYPE: PRT
<213> ORGANISM: Homo sapiens
<220> FEATURE:
<221> NAME/KEY: DOMAIN
<222> LOCATION: (1)...(12)
<223> OTHER INFORMATION: Fragment of Human Factor VIII Protein from Glu
      181 through Leu 192

<400> SEQUENCE: 11

Glu Gly Ser Leu Ala Lys Glu Lys Thr Gln Thr Leu
1               5                   10

<210> SEQ ID NO 12
<211> LENGTH: 16
<212> TYPE: PRT
<213> ORGANISM: Homo sapiens
<220> FEATURE:
```

```
<221> NAME/KEY: DOMAIN
<222> LOCATION: (1)...(16)
<223> OTHER INFORMATION: Fragment of Human Factor VIII Protein from Asp
      203 through Gln 218

<400> SEQUENCE: 12

Asp Glu Gly Lys Ser Trp His Ser Glu Thr Lys Asn Ser Leu Met Gln
1               5                   10                  15

<210> SEQ ID NO 13
<211> LENGTH: 29
<212> TYPE: PRT
<213> ORGANISM: Homo sapiens
<220> FEATURE:
<221> NAME/KEY: DOMAIN
<222> LOCATION: (1)...(29)
<223> OTHER INFORMATION: Fragment of Human Factor VIII Protein from Asp
      327 through Met 355

<400> SEQUENCE: 13

Asp Ser Cys Pro Glu Glu Pro Gln Leu Arg Met Lys Asn Asn Glu Glu
                5                   10                  15

Ala Glu Asp Tyr Asp Asp Asp Leu Thr Asp Ser Glu Met
                    20                  25

<210> SEQ ID NO 14
<211> LENGTH: 23
<212> TYPE: PRT
<213> ORGANISM: Homo sapiens
<220> FEATURE:
<221> NAME/KEY: DOMAIN
<222> LOCATION: (1)...(23)
<223> OTHER INFORMATION: Fragment of Human Factor VIII Protein from Asp
      403 through Lys 425

<400> SEQUENCE: 14

Asp Asp Arg Ser Tyr Lys Ser Gln Tyr Leu Asn Asn Gly Pro Gln Arg
                5                   10                  15

Ile Gly Arg Lys Tyr Lys Lys
                    20

<210> SEQ ID NO 15
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: Fragment of Human Factor VIII Protein from Val
      517 through Arg 527

<400> SEQUENCE: 15

Val Glu Asp Gly Pro Thr Lys Ser Asp Pro Arg
1               5                   10

<210> SEQ ID NO 16
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: Fragment of Human Factor VIII Protein from His
      693 through Gly 701

<400> SEQUENCE: 16

His Asn Ser Asp Phe Arg Asn Arg Gly
1               5
```

```
<210> SEQ ID NO 17
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: Fragment of Human Factor VIII Protein from Ser
      710 through Asp 725

<400> SEQUENCE: 17

Ser Cys Asp Lys Asn Thr Gly Asp Tyr Tyr Glu Asp Ser Tyr Glu Asp
1               5                   10                  15

<210> SEQ ID NO 18
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: Fragment of Human Factor VIII Protein from Lys
      2085 through Phe 2093

<400> SEQUENCE: 18

Lys Thr Gln Gly Ala Arg Gln Lys Phe
1               5

<210> SEQ ID NO 19
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: Fragment of Human Factor VIII Protein from Asp
      2108 through Gly 2121

<400> SEQUENCE: 19

Asp Gly Lys Lys Trp Gln Thr Tyr Arg Gly Asn Ser Thr Gly
1               5                   10

<210> SEQ ID NO 20
<211> LENGTH: 8
<212> TYPE: PRT
<213> ORGANISM: Homo sapiens
<220> FEATURE:
<221> NAME/KEY: DOMAIN
<222> LOCATION: (1)...(8)
<223> OTHER INFORMATION: Fragment of Human Factor VIII Protein from Gly
      2242 through Lys 2249

<400> SEQUENCE: 20

Gly Val Thr Thr Gln Gly Val Lys
1               5

<210> SEQ ID NO 21
<211> LENGTH: 2351
<212> TYPE: PRT
<213> ORGANISM: Homo sapiens
<220> FEATURE:
<221> NAME/KEY: SIGNAL
<222> LOCATION: (1)...(19)

<400> SEQUENCE: 21

Met Gln Ile Glu Leu Ser Thr Cys Phe Phe Leu Cys Leu Leu Arg Phe
        -15                 -10                 -5
```

-continued

```
Cys Phe Ser Ala Thr Arg Arg Tyr Tyr Leu Gly Ala Val Glu Leu Ser
 1               5                  10

Trp Asp Tyr Met Gln Ser Asp Leu Gly Glu Leu Pro Val Asp Ala Arg
     15              20              25

Phe Pro Pro Arg Val Pro Lys Ser Phe Pro Phe Asn Thr Ser Val Val
 30              35              40              45

Tyr Lys Lys Thr Leu Phe Val Glu Phe Thr Asp His Leu Phe Asn Ile
             50              55              60

Ala Lys Pro Arg Pro Pro Trp Met Gly Leu Leu Gly Pro Thr Ile Gln
             65              70              75

Ala Glu Val Tyr Asp Thr Val Val Ile Thr Leu Lys Asn Met Ala Ser
         80              85              90

His Pro Val Ser Leu His Ala Val Gly Val Ser Tyr Trp Lys Ala Ser
     95              100             105

Glu Gly Ala Glu Tyr Asp Asp Gln Thr Ser Gln Arg Glu Lys Glu Asp
110             115             120             125

Asp Lys Val Phe Pro Gly Gly Ser His Thr Tyr Val Trp Gln Val Leu
             130             135             140

Lys Glu Asn Gly Pro Met Ala Ser Asp Pro Leu Cys Leu Thr Tyr Ser
             145             150             155

Tyr Leu Ser His Val Asp Leu Val Lys Asp Leu Asn Ser Gly Leu Ile
         160             165             170

Gly Ala Leu Leu Val Cys Arg Glu Gly Ser Leu Ala Lys Glu Lys Thr
     175             180             185

Gln Thr Leu His Lys Phe Ile Leu Leu Phe Ala Val Phe Asp Glu Gly
190             195             200             205

Lys Ser Trp His Ser Glu Thr Lys Asn Ser Leu Met Gln Asp Arg Asp
             210             215             220

Ala Ala Ser Ala Arg Ala Trp Pro Lys Met His Thr Val Asn Gly Tyr
             225             230             235

Val Asn Arg Ser Leu Pro Gly Leu Ile Gly Cys His Arg Lys Ser Val
         240             245             250

Tyr Trp His Val Ile Gly Met Gly Thr Thr Pro Glu Val His Ser Ile
     255             260             265

Phe Leu Glu Gly His Thr Phe Leu Val Arg Asn His Arg Gln Ala Ser
270             275             280             285

Leu Glu Ile Ser Pro Ile Thr Phe Leu Thr Ala Gln Thr Leu Leu Met
             290             295             300

Asp Leu Gly Gln Phe Leu Leu Phe Cys His Ile Ser Ser His Gln His
             305             310             315

Asp Gly Met Glu Ala Tyr Val Lys Val Asp Ser Cys Pro Glu Glu Pro
         320             325             330

Gln Leu Arg Met Lys Asn Asn Glu Glu Ala Glu Asp Tyr Asp Asp Asp
     335             340             345

Leu Thr Asp Ser Glu Met Asp Val Val Arg Phe Asp Asp Asp Asn Ser
350             355             360             365

Pro Ser Phe Ile Gln Ile Arg Ser Val Ala Lys Lys His Pro Lys Thr
             370             375             380

Trp Val His Tyr Ile Ala Ala Glu Glu Glu Asp Trp Asp Tyr Ala Pro
             385             390             395

Leu Val Leu Ala Pro Asp Asp Arg Ser Tyr Lys Ser Gln Tyr Leu Asn
         400             405             410

Asn Gly Pro Gln Arg Ile Gly Arg Lys Tyr Lys Lys Val Arg Phe Met
```

|   |   |   | 415 |   |   |   | 420 |   |   |   | 425 |   |
|---|---|---|---|---|---|---|---|---|---|---|---|---|

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Val Gly Asp Thr Leu
            450                 455                 460

Leu Ile Ile Phe Lys Asn Gln Ala Ser Arg Pro Tyr Asn Ile Tyr Pro
            465                 470                 475

His Gly Ile Thr Asp Val Arg Pro Leu Tyr Ser Arg Leu Pro Lys
            480                 485                 490

Gly Val Lys His Leu Lys Asp Phe Pro Ile Leu Pro Gly Glu Ile Phe
495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
            530                 535                 540

Asp Leu Ala Ser Gly Leu Ile Gly Pro Leu Leu Ile Cys Tyr Lys Glu
                545                 550                 555

Ser Val Asp Gln Arg Gly Asn Gln Ile Met Ser Asp Lys Arg Asn Val
            560                 565                 570

Ile Leu Phe Ser Val Phe Asp Glu Asn Arg Ser Trp Tyr Leu Thr Glu
            575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
            625                 630                 635

Tyr Ile Leu Ser Ile Gly Ala Gln Thr Asp Phe Leu Ser Val Phe Phe
            640                 645                 650

Ser Gly Tyr Thr Phe Lys His Lys Met Val Tyr Glu Asp Thr Leu Thr
            655                 660                 665

Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
            690                 695                 700

Met Thr Ala Leu Leu Lys Val Ser Ser Cys Asp Lys Asn Thr Gly Asp
                705                 710                 715

Tyr Tyr Glu Asp Ser Tyr Glu Asp Ile Ser Ala Tyr Leu Leu Ser Lys
            720                 725                 730

Asn Asn Ala Ile Glu Pro Arg Ser Phe Ser Gln Asn Ser Arg His Pro
735                 740                 745

Ser Thr Arg Gln Lys Gln Phe Asn Ala Thr Thr Ile Pro Glu Asn Asp
750                 755                 760                 765

Ile Glu Lys Thr Asp Pro Trp Phe Ala His Arg Thr Pro Met Pro Lys
            770                 775                 780

Ile Gln Asn Val Ser Ser Ser Asp Leu Leu Met Leu Leu Arg Gln Ser
            785                 790                 795

Pro Thr Pro His Gly Leu Ser Leu Ser Asp Leu Gln Glu Ala Lys Tyr
            800                 805                 810

Glu Thr Phe Ser Asp Asp Pro Ser Pro Gly Ala Ile Asp Ser Asn Asn
            815                 820                 825

Ser Leu Ser Glu Met Thr His Phe Arg Pro Gln Leu His His Ser Gly
830                 835                 840                 845

-continued

```
Asp Met Val Phe Thr Pro Glu Ser Gly Leu Gln Leu Arg Leu Asn Glu
            850                 855                 860
Lys Leu Gly Thr Thr Ala Ala Thr Glu Leu Lys Lys Leu Asp Phe Lys
            865                 870                 875
Val Ser Thr Ser Asn Asn Leu Ile Ser Thr Ile Pro Ser Asp Asn
        880                 885                 890
Leu Ala Ala Gly Thr Asp Asn Thr Ser Ser Leu Gly Pro Pro Ser Met
    895                 900                 905
Pro Val His Tyr Asp Ser Gln Leu Asp Thr Thr Leu Phe Gly Lys Lys
910                 915                 920                 925
Ser Ser Pro Leu Thr Glu Ser Gly Pro Leu Ser Leu Ser Glu Glu
                930                 935                 940
Asn Asn Asp Ser Lys Leu Leu Glu Ser Gly Leu Met Asn Ser Gln Glu
            945                 950                 955
Ser Ser Trp Gly Lys Asn Val Ser Ser Thr Glu Ser Gly Arg Leu Phe
            960                 965                 970
Lys Gly Lys Arg Ala His Gly Pro Ala Leu Leu Thr Lys Asp Asn Ala
    975                 980                 985
Leu Phe Lys Val Ser Ile Ser Leu Leu Lys Thr Asn Lys Thr Ser Asn
990                 995                 1000                1005
Asn Ser Ala Thr Asn Arg Lys Thr His Ile Asp Gly Pro Ser Leu Leu
            1010                1015                1020
Ile Glu Asn Ser Pro Ser Val Trp Gln Asn Ile Leu Glu Ser Asp Thr
            1025                1030                1035
Glu Phe Lys Lys Val Thr Pro Leu Ile His Asp Arg Met Leu Met Asp
            1040                1045                1050
Lys Asn Ala Thr Ala Leu Arg Leu Asn His Met Ser Asn Lys Thr Thr
            1055                1060                1065
Ser Ser Lys Asn Met Glu Met Val Gln Lys Lys Glu Gly Pro Ile
1070                1075                1080                1085
Pro Pro Asp Ala Gln Asn Pro Asp Met Ser Phe Phe Lys Met Leu Phe
            1090                1095                1100
Leu Pro Glu Ser Ala Arg Trp Ile Gln Arg Thr His Gly Lys Asn Ser
            1105                1110                1115
Leu Asn Ser Gly Gln Gly Pro Ser Pro Lys Gln Leu Val Ser Leu Gly
            1120                1125                1130
Pro Glu Lys Ser Val Glu Gly Gln Asn Phe Leu Ser Glu Lys Asn Lys
            1135                1140                1145
Val Val Val Gly Lys Gly Glu Phe Thr Lys Asp Val Gly Leu Lys Glu
1150                1155                1160                1165
Met Val Phe Pro Ser Ser Arg Asn Leu Phe Leu Thr Asn Leu Asp Asn
            1170                1175                1180
Leu His Glu Asn Asn Thr His Asn Gln Glu Lys Lys Ile Gln Glu Glu
            1185                1190                1195
Ile Glu Lys Lys Glu Thr Leu Ile Gln Glu Asn Val Val Leu Pro Gln
            1200                1205                1210
Ile His Thr Val Thr Gly Thr Lys Asn Phe Met Lys Asn Leu Phe Leu
    1215                1220                1225
Leu Ser Thr Arg Gln Asn Val Glu Gly Ser Tyr Asp Gly Ala Tyr Ala
1230                1235                1240                1245
Pro Val Leu Gln Asp Phe Arg Ser Leu Asn Asp Ser Thr Asn Arg Thr
            1250                1255                1260
```

-continued

Lys Lys His Thr Ala His Phe Ser Lys Lys Gly Glu Glu Asn Leu
            1265                1270                1275

Glu Gly Leu Gly Asn Gln Thr Lys Gln Ile Val Glu Lys Tyr Ala Cys
        1280                1285                1290

Thr Thr Arg Ile Ser Pro Asn Thr Ser Gln Gln Asn Phe Val Thr Gln
    1295                1300                1305

Arg Ser Lys Arg Ala Leu Lys Gln Phe Arg Leu Pro Leu Glu Thr
1310                1315                1320                1325

Glu Leu Glu Lys Arg Ile Ile Val Asp Asp Thr Ser Thr Gln Trp Ser
            1330                1335                1340

Lys Asn Met Lys His Leu Thr Pro Ser Thr Leu Thr Gln Ile Asp Tyr
        1345                1350                1355

Asn Glu Lys Glu Lys Gly Ala Ile Thr Gln Ser Pro Leu Ser Asp Cys
    1360                1365                1370

Leu Thr Arg Ser His Ser Ile Pro Gln Ala Asn Arg Ser Pro Leu Pro
    1375                1380                1385

Ile Ala Lys Val Ser Ser Phe Pro Ser Ile Arg Pro Ile Tyr Leu Thr
1390                1395                1400                1405

Arg Val Leu Phe Gln Asp Asn Ser Ser His Leu Pro Ala Ala Ser Tyr
            1410                1415                1420

Arg Lys Lys Asp Ser Gly Val Gln Glu Ser Ser His Phe Leu Gln Gly
        1425                1430                1435

Ala Lys Lys Asn Asn Leu Ser Leu Ala Ile Leu Thr Leu Glu Met Thr
    1440                1445                1450

Gly Asp Gln Arg Glu Val Gly Ser Leu Gly Thr Ser Ala Thr Asn Ser
    1455                1460                1465

Val Thr Tyr Lys Lys Val Glu Asn Thr Val Leu Pro Lys Pro Asp Leu
1470                1475                1480                1485

Pro Lys Thr Ser Gly Lys Val Glu Leu Leu Pro Lys Val His Ile Tyr
            1490                1495                1500

Gln Lys Asp Leu Phe Pro Thr Glu Thr Ser Asn Gly Ser Pro Gly His
        1505                1510                1515

Leu Asp Leu Val Glu Gly Ser Leu Leu Gln Gly Thr Glu Gly Ala Ile
        1520                1525                1530

Lys Trp Asn Glu Ala Asn Arg Pro Gly Lys Val Pro Phe Leu Arg Val
    1535                1540                1545

Ala Thr Glu Ser Ser Ala Lys Thr Pro Ser Lys Leu Leu Asp Pro Leu
1550                1555                1560                1565

Ala Trp Asp Asn His Tyr Gly Thr Gln Ile Pro Lys Glu Glu Trp Lys
            1570                1575                1580

Ser Gln Glu Lys Ser Pro Glu Lys Thr Ala Phe Lys Lys Lys Asp Thr
        1585                1590                1595

Ile Leu Ser Leu Asn Ala Cys Glu Ser Asn His Ala Ile Ala Ala Ile
    1600                1605                1610

Asn Glu Gly Gln Asn Lys Pro Glu Ile Glu Val Thr Trp Ala Lys Gln
    1615                1620                1625

Gly Arg Thr Glu Arg Leu Cys Ser Gln Asn Pro Pro Val Leu Lys Arg
1630                1635                1640                1645

His Gln Arg Glu Ile Thr Arg Thr Thr Leu Gln Ser Asp Gln Glu Glu
            1650                1655                1660

Ile Asp Tyr Asp Asp Thr Ile Ser Val Glu Met Lys Lys Glu Asp Phe
        1665                1670                1675

Asp Ile Tyr Asp Glu Asp Glu Asn Gln Ser Pro Arg Ser Phe Gln Lys

-continued

```
                 1680                1685                1690
Lys Thr Arg His Tyr Phe Ile Ala Ala Val Glu Arg Leu Trp Asp Tyr
        1695                1700                1705
Gly Met Ser Ser Pro His Val Leu Arg Asn Arg Ala Gln Ser Gly
1710                1715                1720                1725
Ser Val Pro Gln Phe Lys Val Val Phe Gln Glu Phe Thr Asp Gly
                1730                1735                1740
Ser Phe Thr Gln Pro Leu Tyr Arg Gly Glu Leu Asn Glu His Leu Gly
                1745                1750                1755
Leu Leu Gly Pro Tyr Ile Arg Ala Glu Val Asp Asn Ile Met Val
            1760                1765                1770
Thr Phe Arg Asn Gln Ala Ser Arg Pro Tyr Ser Phe Tyr Ser Ser Leu
        1775                1780                1785
Ile Ser Tyr Glu Glu Asp Gln Arg Gln Gly Ala Glu Pro Arg Lys Asn
1790                1795                1800                1805
Phe Val Lys Pro Asn Glu Thr Lys Thr Tyr Phe Trp Lys Val Gln His
                1810                1815                1820
His Met Ala Pro Thr Lys Asp Glu Phe Asp Cys Lys Ala Trp Ala Tyr
            1825                1830                1835
Phe Ser Asp Val Asp Leu Glu Lys Asp Val His Ser Gly Leu Ile Gly
        1840                1845                1850
Pro Leu Leu Val Cys His Thr Asn Thr Leu Asn Pro Ala His Gly Arg
        1855                1860                1865
Gln Val Thr Val Gln Glu Phe Ala Leu Phe Phe Thr Ile Phe Asp Glu
1870                1875                1880                1885
Thr Lys Ser Trp Tyr Phe Thr Glu Asn Met Glu Arg Asn Cys Arg Ala
                1890                1895                1900
Pro Cys Asn Ile Gln Met Glu Asp Pro Thr Phe Lys Glu Asn Tyr Arg
            1905                1910                1915
Phe His Ala Ile Asn Gly Tyr Ile Met Asp Thr Leu Pro Gly Leu Val
            1920                1925                1930
Met Ala Gln Asp Gln Arg Ile Arg Trp Tyr Leu Leu Ser Met Gly Ser
        1935                1940                1945
Asn Glu Asn Ile His Ser Ile His Phe Ser Gly His Val Phe Thr Val
1950                1955                1960                1965
Arg Lys Lys Glu Glu Tyr Lys Met Ala Leu Tyr Asn Leu Tyr Pro Gly
                1970                1975                1980
Val Phe Glu Thr Val Glu Met Leu Pro Ser Lys Ala Gly Ile Trp Arg
            1985                1990                1995
Val Glu Cys Leu Ile Gly Glu His Leu His Ala Gly Met Ser Thr Leu
        2000                2005                2010
Phe Leu Val Tyr Ser Asn Lys Cys Gln Thr Pro Leu Gly Met Ala Ser
    2015                2020                2025
Gly His Ile Arg Asp Phe Gln Ile Thr Ala Ser Gly Gln Tyr Gly Gln
2030                2035                2040                2045
Trp Ala Pro Lys Leu Ala Arg Leu His Tyr Ser Gly Ser Ile Asn Ala
                2050                2055                2060
Trp Ser Thr Lys Glu Pro Phe Ser Trp Ile Lys Val Asp Leu Leu Ala
            2065                2070                2075
Pro Met Ile Ile His Gly Ile Lys Thr Gln Gly Ala Arg Gln Lys Phe
        2080                2085                2090
Ser Ser Leu Tyr Ile Ser Gln Phe Ile Ile Met Tyr Ser Leu Asp Gly
        2095                2100                2105
```

-continued

```
Lys Lys Trp Gln Thr Tyr Arg Gly Asn Ser Thr Gly Thr Leu Met Val
2110                2115                2120                2125

Phe Phe Gly Asn Val Asp Ser Ser Gly Ile Lys His Asn Ile Phe Asn
            2130                2135                2140

Pro Pro Ile Ile Ala Arg Tyr Ile Arg Leu His Pro Thr His Tyr Ser
            2145                2150                2155

Ile Arg Ser Thr Leu Arg Met Glu Leu Met Gly Cys Asp Leu Asn Ser
        2160                2165                2170

Cys Ser Met Pro Leu Gly Met Glu Ser Lys Ala Ile Ser Asp Ala Gln
    2175                2180                2185

Ile Thr Ala Ser Ser Tyr Phe Thr Asn Met Phe Ala Thr Trp Ser Pro
2190                2195                2200                2205

Ser Lys Ala Arg Leu His Leu Gln Gly Arg Ser Asn Ala Trp Arg Pro
            2210                2215                2220

Gln Val Asn Asn Pro Lys Glu Trp Leu Gln Val Asp Phe Gln Lys Thr
            2225                2230                2235

Met Lys Val Thr Gly Val Thr Thr Gln Gly Val Lys Ser Leu Leu Thr
            2240                2245                2250

Ser Met Tyr Val Lys Glu Phe Leu Ile Ser Ser Ser Gln Asp Gly His
    2255                2260                2265

Gln Trp Thr Leu Phe Phe Gln Asn Gly Lys Val Lys Val Phe Gln Gly
2270                2275                2280                2285

Asn Gln Asp Ser Phe Thr Pro Val Val Asn Ser Leu Asp Pro Pro Leu
            2290                2295                2300

Leu Thr Arg Tyr Leu Arg Ile His Pro Gln Ser Trp Val His Gln Ile
            2305                2310                2315

Ala Leu Arg Met Glu Val Leu Gly Cys Glu Ala Gln Asp Leu Tyr
            2320                2325                2330
```